(12) United States Patent
Fujita et al.

(10) Patent No.: US 10,420,513 B2
(45) Date of Patent: Sep. 24, 2019

(54) BIOLOGICAL STATE ESTIMATION DEVICE, BIOLOGICAL STATE ESTIMATION METHOD, COMPUTER PROGRAM, AND RECORDING MEDIUM

(71) Applicant: DELTA KOGYO CO., LTD., Aki-gun (JP)

(72) Inventors: Etsunori Fujita, Higashihiroshima (JP); Yumi Ogura, Higashihiroshima (JP); Yoshika Nobuhiro, Hiroshima (JP)

(73) Assignee: DELTA KOGYO CO., LTD., Aki-gun (JP)

( * ) Notice: Subject to any disclaimer, the term of this patent is extended or adjusted under 35 U.S.C. 154(b) by 0 days.

(21) Appl. No.: 16/061,243

(22) PCT Filed: Dec. 12, 2016

(86) PCT No.: PCT/JP2016/086959
§ 371 (c)(1),
(2) Date: Jun. 11, 2018

(87) PCT Pub. No.: WO2017/099257
PCT Pub. Date: Jun. 15, 2017

(65) Prior Publication Data
US 2018/0360389 A1    Dec. 20, 2018

(30) Foreign Application Priority Data

Dec. 12, 2015 (JP) ................................ 2015-242757

(51) Int. Cl.
*A61B 5/00* (2006.01)
*A61B 5/02* (2006.01)
(Continued)

(52) U.S. Cl.
CPC .............. *A61B 5/7246* (2013.01); *A61B 5/00* (2013.01); *A61B 5/02* (2013.01); *A61B 5/0402* (2013.01);
(Continued)

(58) Field of Classification Search
CPC combination set(s) only.
See application file for complete search history.

(56) References Cited

U.S. PATENT DOCUMENTS

| 9,706,955 B2 * | 7/2017 | Atsumori | ............. A61B 5/7475 |
| 10,271,087 B2 * | 4/2019 | Klappert | ................. G06F 3/015 |

(Continued)

FOREIGN PATENT DOCUMENTS

| JP | 2009-78139 A | 4/2009 |
| JP | 2009-95511 A | 5/2009 |

(Continued)

OTHER PUBLICATIONS

Extended European Search Report dated Sep. 13, 2018 in the corresponding European Application No. 16873149.5 citing documents AA, AO, AX and AY therein 11 pages.

(Continued)

*Primary Examiner* — Travis R Hunnings
(74) *Attorney, Agent, or Firm* — Oblon, McClelland, Maier & Neustadt, L.L.P.

(57) ABSTRACT

The present invention is configured to compare an output result of frequency analysis of a frequency gradient time-series waveform of a biosignal with preset corresponding data of output results of brain waves of different biological states to the output result. Accordingly, it is possible to estimate a time-series variation of a biological state which is specified by a brain wave state and brain waves by using a biological index other than brain waves, in particular, a result of frequency analysis of a frequency gradient time-
(Continued)

series waveform of a biosignal reflecting an autonomic nervous function. Using an electroencephalograph is not required, and thus it is possible to estimate brain waves and a biological state corresponding to brain waves easily and rapidly.

12 Claims, 17 Drawing Sheets

(51) Int. Cl.
| | |
|---|---|
| A61B 5/0452 | (2006.01) |
| A61B 5/0476 | (2006.01) |
| A61B 5/11 | (2006.01) |
| A61B 5/0402 | (2006.01) |
| G16H 50/30 | (2018.01) |
| G16H 40/63 | (2018.01) |
| G16H 20/70 | (2018.01) |
| A61B 5/024 | (2006.01) |
| A61B 5/04 | (2006.01) |

(52) U.S. Cl.
CPC .......... *A61B 5/0452* (2013.01); *A61B 5/0476* (2013.01); *A61B 5/11* (2013.01); *A61B 5/4809* (2013.01); *A61B 5/4812* (2013.01); *A61B 5/7275* (2013.01); *G16H 20/70* (2018.01); *G16H 40/63* (2018.01); *G16H 50/30* (2018.01); *A61B 5/02416* (2013.01); *A61B 5/04014* (2013.01); *A61B 5/7253* (2013.01); *A61B 2562/02* (2013.01)

(56) References Cited

U.S. PATENT DOCUMENTS

| | | |
|---|---|---|
| 2009/0143654 A1 | 6/2009 | Funane et al. |
| 2012/0259181 A1 | 10/2012 | Fujita et al. |
| 2013/0030256 A1 | 1/2013 | Fujita et al. |
| 2013/0225940 A1 | 8/2013 | Fujita et al. |
| 2015/0327803 A1 | 11/2015 | Fujita et al. |

FOREIGN PATENT DOCUMENTS

| | | |
|---|---|---|
| JP | 2011-167362 A | 9/2011 |
| JP | 2012-179202 A | 9/2012 |
| JP | 2012-239480 A | 12/2012 |
| JP | 2014-117425 A | 6/2014 |
| JP | 2014-223271 A | 12/2014 |
| JP | 2014-230717 A | 12/2014 |
| WO | WO 2011/046178 A1 | 4/2011 |

OTHER PUBLICATIONS

Abdullah, H., et al., "Cross-correlation of EEG frequency bands and heart rate variability for sleep apnoea classification", Medical & Biological Engineering & Computing, Springer, Berlin, DE, vol. 48, No. 12, XP019865762, Nov. 3, 2010, pp. 1261-1269.

Chiu, Hung-Chin, et al., "Complexity of cardiac signals for predicting changes in alpha-waves after stress in patients undergoing cardiac catheterization", Scientific Reports, Vo. 5, No. 1, XP055502460, Aug. 19, 2015, 14 pages.

International Search Report dated Feb. 28, 2017, in PCT/JP2016/086959, filed Dec. 12, 2016.

* cited by examiner

BIOLOGICAL STATE ESTIMATION DEVICE, BIOLOGICAL STATE ESTIMATION METHOD, COMPUTER PROGRAM, AND RECORDING MEDIUM

TECHNICAL FIELD

The present invention relates to a biological state estimation device which estimates a biological state of a person, which is specified by brain waves, based on a biosignal of the person measured by a biosignal measurement device, a biological state estimation method therefor, and a computer program therefor, and a recording medium.

BACKGROUND ART

In Patent Documents 1 to 5 and so on, the present inventors have proposed an art to detect vibration generated on the body surface of the back in the upper body of a person by a biosignal measurement device and analyze the state of the person. Sound and vibration information arising from motions of the heart and the aorta, which is detected from the back of the upper body of the person, is pressure vibration arising from the motions of the heart and the aorta, and includes information on the systole and diastole of the ventricles, information on vascular wall elasticity which serves as an auxiliary pump for the circulation, and information on reflected waves. That is, the sound and vibration information includes information on a back body surface pulse wave (including an Aortic Pulse Wave (APW)) of around 1 Hz generated on the back surface due to the motions of the heart and the aorta and information on sound conveyed to the back side in accordance with heartbeat ("pseudo heart sound" (in this specification, sound of the heart collected from the back side is referred to as "pseudo heart sound", in contrast to heart sound which is sound of the heart collected from the chest side). Then, a signal waveform accompanying heart rate variability includes information on neural activities of the sympathetic nervous system and the parasympathetic nervous system, and a signal waveform accompanying aortic oscillation includes information on sympathetic nerve activity.

In Patent Document 1, slide calculation is performed in which a predetermined time width is set in a time-series waveform of back body surface pulse waves (APW) of around 1 Hz extracted from collected biosignals (sound and vibration information), to obtain a frequency gradient time-series waveform, and according to the tendency of its variation, for example, according to whether its amplitude is on the decrease or the increase, a biological state is estimated. It is also disclosed that, by frequency analysis of the biosignal, power spectra of respective frequencies corresponding to predetermined signals such as a function regulation signal, a fatigue reception signal, and an activity regulation signal belonging to a ULF band (ultra low-frequency band) to a VLF band (very low-frequency band) are obtained, and the state of a person is judged from time-series variations of the respective power spectra. Since the fatigue reception signal indicates a progress degree of fatigue in a normal active state, additionally comparing predominant degrees of the power spectra of the function regulation signal and the activity regulation signal makes it possible to judge the state of a person (a sympathetic nerve predominant state, a parasympathetic nerve predominant state, or the like). It is further disclosed that, with the total value of the power spectra of frequency components corresponding to these three signals being set as 100, time-series distribution ratios of the respective frequency components are obtained, and the state of a person is judged using time-series variations of the distribution ratios.

As a method of quantifying a biological state, Patent Document 2 proposes an art to represent the biological state as a physical condition map and a sensation map. To create them, the above-described APW is frequency-analyzed, an analyzed waveform in each target analysis section is displayed on log-log axes, the analyzed waveform is classified into a low-frequency band, an intermediate-frequency band, or a high-frequency band, and according to a gradient of the classified analyzed waveform and the shape of the whole analyzed waveform, the analyzed waveform is scored based on a predetermined criterion, and the results are plotted on coordinate axes. The physical condition map shows the control state of the autonomic nervous system from a viewpoint of the balance between the sympathetic nerve and the parasympathetic nerve, and in the sensation map, the state of a change of heart rate variability is superimposed on the physical condition map.

Patent Documents 3 to 5 disclose a means for judging a homeostasis function level. For the judgment, the means for judging the homeostasis function level uses at least one or more of plus/minus of a differentiated waveform of a frequency gradient time-series waveform, plus/minus of an integrated waveform obtained by integrating the frequency gradient time-series waveform, absolute values of frequency gradient time-series waveforms obtained by absolute value processing of a frequency gradient time-series waveform obtained by a zero-cross method and a frequency gradient time-series waveform obtained by a peak detection method, and so on. By using the combination of these, it is obtained on which level the homeostasis function is. For example, the level can be set such that, when the frequency gradient and the integrated value are used and they are predetermined values or more, it is judged that "the homeostasis function level is 1," or when the differential value is equal to or less than a predetermined value and "peak is predominant" out of the two absolute values, it is judged that "the homeostasis function level is 4." The combination of these, a threshold value for the judgment, and so on are determined based on the results of statistical processing of data of many subjects.

Non-patent Document 1 discloses an art to obtain, regarding finger plethysmogram information, a frequency gradient time-series waveform of a power value reflecting information on the sympathetic nerve, and plot integrated values resulting from absolute value processing of this, in a time-series manner as a fatigue degree to depict a fatigue curve, from which muscle fatigue is obtained. Non-patent Document 2 discloses an art to arithmetically process biosignals which are obtained from the back of a person using an air pack sensor, to depict a fatigue curve by a similar method and grasp muscle fatigue. That is, it is possible to grasp the state of the muscle fatigue by using a frequency gradient time-series waveform (a frequency gradient time-series waveform by a zero-cross method in the case of APW) of a power value reflecting information on the sympathetic nerve.

PRIOR ART DOCUMENT

Patent Document

Patent Document 1: Japanese Patent Application Laid-open No. 2011-167362
Patent Document 2: Japanese Patent Application Laid-open No. 2012-239480

Patent Document 3: WO2011/046178
Patent Document 4: Japanese Patent Application Laid-open No. 2014-117425
Patent Document 5: Japanese Patent Application Laid-open No. 2014-223271

Non-Patent Document

Non-patent Document 1: "Development of simplified appraisal method of fatigue on sitting for extended periods by the data of finger plethysmogram," Etsunori FUJITA (eight others), Ergonomics Vol. 40, No. 5 ('04)

Non-patent Document 2: "Application of biological fluctuation signals measured by non-invasive sensor to fatigue and hypnagogia prediction," Naoki OCHIAI (six others), The 39th Japan Ergonomics Society, Chugoku-Shikoku Branch Conference, Proceedings, issued on Nov. 25, 2006, publishing office: Japan Ergonomics Society Chugoku-Shikoku branch office

SUMMARY OF THE INVENTION

Problems to be Solved by the Invention

All of the above-described arts judge the state of a person by analyzing elements which vary due to fluctuations of the bioregulation functions, and are excellent in the point capable of detecting various biological states such as a hypnagogic symptom phenomenon, an imminent sleep phenomenon, a low consciousness traveling state, a homeostasis function level, an initial fatigue state, and feeling judgment. In the meantime, the brain waves are a highly reliable index as one to estimate the state of a person such as a sleep stage, but require attachment of an electroencephalograph, which takes a lot of trouble with measurement.

The present invention was made in consideration of the above, and has an object to provide a biological state estimation device suitable for estimating a biological state to be specified by a brain wave state and brain waves while using a biological index other than brain waves to be measured by an electroencephalograph, a biological state estimation method therefor, a computer program therefor, and a recording medium.

Means for Solving the Problems

In order to solve the above-described problems, the biological state estimation device of the present invention is a biological state estimation device which estimates a biological state by using a biosignal, the biological state estimation device including:

a frequency gradient time-series waveform calculation means which, from time-series data of the biosignal, obtains a time-series fluctuation of a frequency and obtains a gradient in a predetermined time range of the time-series fluctuation of the frequency, and obtains a time-series fluctuation of the gradient as a frequency gradient time-series waveform;

a frequency analysis means which frequency-analyzes the frequency gradient time-series waveform every predetermined time range; and an estimation means which compares an output result of the frequency analysis obtained by the frequency analysis means every predetermined time range with preset corresponding data of output results of brain waves of different biological states to the output result of the frequency analysis and estimates a time-series variation of a biological state which is specified by a state of the brain wave and brain waves by means of a time-series variation of the output result of the frequency analysis.

Preferably, the frequency analysis means outputs the result of the frequency analysis in at least one graph of a log-log graph and a linear graph each between frequency and power spectrum density, and the estimation means uses an output result represented by at least one of the log-log graph and the linear graph, compares the output result with the corresponding data of the brain wave, and estimates a biological state which is specified by a state of the brain wave and brain waves.

Preferably, in the case where the log-log graph is used as an output result of frequency analysis obtained by the frequency analysis means, the estimation means is set to estimate that the case where an approximate line of an analyzed waveform represented by the log-log graph is approximate to 1/f is a "sleep state" where in brain wave distribution ratios, the θ wave is predominant over the α wave, the θ wave is equal to or more than predetermined values, and the α wave is equal to or less than predetermined values, and estimate that the case where the approximate line is approximate to $1/f^2$ is a "state of sleepiness strongly resisting while being in a wakeful state" where the α wave or the β wave is the same as or predominant over the θ wave and the distribution ratio of β wave is the same as or predominant over the distribution ratio of θ wave when compared.

Preferably, in the case where the linear graph is used as an output result of frequency analysis obtained by the frequency analysis means, the estimation means performs estimation by using a position of a predominant frequency or an amplitude of the predominant frequency in the linear graph.

Further, the computer program of the present invention is a computer program causing a computer as a biological state estimation device to execute a biological state estimation procedure for estimating a biological state by analyzing a biosignal of a person measured by a biosignal measurement device, the computer program causing the computer to execute: as the biological state estimation procedure, a frequency gradient time-series waveform calculation procedure which, from time-series data of the biosignal, obtains a time-series fluctuation of a frequency and obtains a gradient in a predetermined time range of the time-series fluctuation of the frequency, and obtains a time-series fluctuation of the gradient as a frequency gradient time-series waveform;

a frequency analysis procedure which frequency-analyzes the frequency gradient time-series waveform every predetermined time range; and an estimation procedure which compares an output result of the frequency analysis obtained by the frequency analysis procedure every predetermined time range with corresponding data of output results of brain waves of different biological states to the output result of the frequency analysis, which are stored in the computer beforehand, and estimates a time-series variation of a biological state which is specified by a state of the brain wave and brain waves by means of a time-series variation of the output result of the frequency analysis.

Preferably, the frequency analysis procedure outputs the result of the frequency analysis in at least one graph of a log-log graph and a linear graph each between frequency and power spectrum density, and the estimation procedure uses an output result represented by at least one of the log-log graph and the linear graph, compares the output result with the corresponding data of the brain wave, and estimates a biological state which is specified by a state of the brain wave and brain waves.

Preferably, in the case where the log-log graph is used as an output result of frequency analysis obtained by execution of the frequency analysis procedure, the estimation procedure estimates that the case where an approximate line of an analyzed waveform represented by the log-log graph is approximate to 1/f is a "sleep state" where in brain wave distribution ratios, the θ wave is predominant over the α wave, the θ wave is equal to or more than predetermined values, and the α wave is equal to or less than predetermined values, and estimates that the case where the approximate line is approximate to $1/f^2$ is a "state of sleepiness strongly resisting while being in a wakeful state" where the α wave or the β wave is the same as or predominant over the θ wave and the distribution ratio of β wave is the same as or predominant over the distribution ratio of θ wave when compared.

Preferably, in the case where the linear graph is used as an output result of frequency analysis obtained by execution of the frequency analysis procedure, the estimation procedure performs estimation by using a position of a predominant frequency or an amplitude of the predominant frequency in the linear graph.

Further, the present invention provides a computer-readable recording medium in which the computer program causing the computer as the biological state estimation device to execute the biological state estimation procedure for estimating the biological state by analyzing the biosignal of a person measured by the biosignal measurement device is recorded.

Further, the biological state estimation method of the present invention is a biological state estimation method which estimates a biological state by using a biosignal, the method including:

from time-series data of the biosignal, obtaining a time-series fluctuation of a frequency and obtaining a gradient in a predetermined time range of the time-series fluctuation of the frequency, and obtaining a time-series fluctuation of the gradient as a frequency gradient time-series waveform;

frequency-analyzing the frequency gradient time-series waveform every predetermined time range; and comparing an output result of the frequency analysis obtained every predetermined time range with preset corresponding data of output results of brain waves of different biological states to the output result of the frequency analysis and estimating a time-series variation of a biological state which is specified by a state of the brain wave and brain waves by means of a time-series variation of the output result of the frequency analysis.

In the biological state estimation method of the present invention, preferably, the result of the frequency analysis is output in at least one graph of a log-log graph and a linear graph each between frequency and power spectrum density, and an output result represented by at least one of the log-log graph and the linear graph is used, to compare the output result with the corresponding data of the brain wave and estimate a biological state which is specified by a state of the brain wave and brain waves. Preferably, in the case where the log-log graph is used as an output result of the frequency analysis, the case where an approximate line of an analyzed waveform represented by the log-log graph is approximate to 1/f is estimated as a "sleep state" where in brain wave distribution ratios, the θ wave is predominant over the α wave, the θ wave is equal to or more than predetermined values, and the α wave is equal to or less than predetermined values, and the case where the approximate line is approximate to $1/f^2$ is estimated as a "state of sleepiness strongly resisting while being in a wakeful state" where the α wave or the β wave is the same as or predominant over the θ wave and the distribution ratio of β wave is the same as or predominant over the distribution ratio of θ wave when compared. Preferably, in the case where the linear graph is used as an output result of the frequency analysis, estimation is performed by using a position of a predominant frequency or an amplitude of the predominant frequency in the linear graph.

Effect of the Invention

According to the present invention, it is configured to compare an output result of frequency analysis of a frequency gradient time-series waveform of a biosignal with preset corresponding data of output results of brain waves of different biological states to the output result. Accordingly, it is possible to estimate a time-series variation of a biological state which is specified by a brain wave state and brain waves by using a biological index other than brain waves, in particular, the result of frequency analysis of a frequency gradient time-series waveform of a biosignal reflecting an autonomic nervous function. Using an electroencephalograph is not required, and thus it is possible to estimate brain waves and a biological state corresponding to brain waves easily and rapidly.

BRIEF DESCRIPTION OF DRAWINGS

FIG. 4(a) is a graph illustrating a sleep stage, FIG. 4(b) is a graph illustrating brain wave distribution ratios (distribution ratios of α wave, β wave, and θ wave), and FIG. 4(c) is a graph illustrating activity levels of the sympathetic nerve (LF/HF) and the parasympathetic nerve (HF) which are calculated from an electrocardiogram.

FIG. 5(a) is a graph of the frequency gradient time-series waveform of a back body surface pulse wave (APW), FIG. 5(b) is a graph of the frequency gradient time-series waveform of a brain wave (EEG), FIG. 5(c) is a graph of the frequency gradient time-series waveform of a heart sound (PCG), FIG. 5(d) is a graph of the frequency gradient time-series waveform of an electrocardiogram (ECG), and FIG. 5(e) is a graph of the frequency gradient time-series waveform of a finger plethysmogram (PPG).

FIG. 8(a) is a graph illustrating a sleep stage, FIG. 8(b) is a graph illustrating brain wave distribution ratios (distribution ratios of α wave, β wave, and θ wave), and FIG. 8(c) is a graph illustrating activity levels of the sympathetic nerve (LF/HF) and the parasympathetic nerve (HF) which are calculated from an electrocardiogram.

FIG. 9(a) is a graph of the frequency gradient time-series waveform of a back body surface pulse wave (APW), FIG. 9(b) is a graph of the frequency gradient time-series waveform of a brain wave (EEG), FIG. 9(c) is a graph of the frequency gradient time-series waveform of a heart sound (PCG), FIG. 9(d) is a graph of the frequency gradient time-series waveform of an electrocardiogram (ECG), and FIG. 9(e) is a graph of the frequency gradient time-series waveform of a finger plethysmogram (PPG).

FIG. 14(a) is a graph illustrating a sleep stage, FIG. 14(b) is a graph illustrating brain wave distribution ratios (distribution ratios of α wave, β wave, and θ wave), and FIG. 14(c) is a graph illustrating activity levels of the sympathetic nerve (LF/HF) and the parasympathetic nerve (HF) which are calculated from an electrocardiogram.

FIG. 15(a) is a graph of the frequency gradient time-series waveform of a back body surface pulse wave (APW), FIG. 15(b) is a graph of the frequency gradient time-series waveform of a brain wave (EEG), FIG. 15(c) is a graph of the frequency gradient time-series waveform of an electrocardiogram (ECG), and FIG. 15(d) is a graph of the frequency gradient time-series waveform of a finger plethysmogram (PPG).

FIG. 16(a) is a graph illustrating a sleep stage, FIG. 16(b) is a graph illustrating brain wave distribution ratios (distribution ratios of α wave, β wave, and θ wave), and FIG. 16(c) is a graph illustrating activity levels of the sympathetic nerve (LF/HF) and the parasympathetic nerve (HF) which are calculated from an electrocardiogram.

FIG. 17(a) is a graph of the frequency gradient time-series waveform of a back body surface pulse wave (APW), FIG. 17(b) is a graph of the frequency gradient time-series waveform of a brain wave (EEG), FIG. 17(c) is a graph of the frequency gradient time-series waveform of an electrocardiogram (ECG), and FIG. 17(d) is a graph of the frequency gradient time-series waveform of a finger plethysmogram (PPG).

MODES FOR CARRYING OUT THE INVENTION

Figure 1:
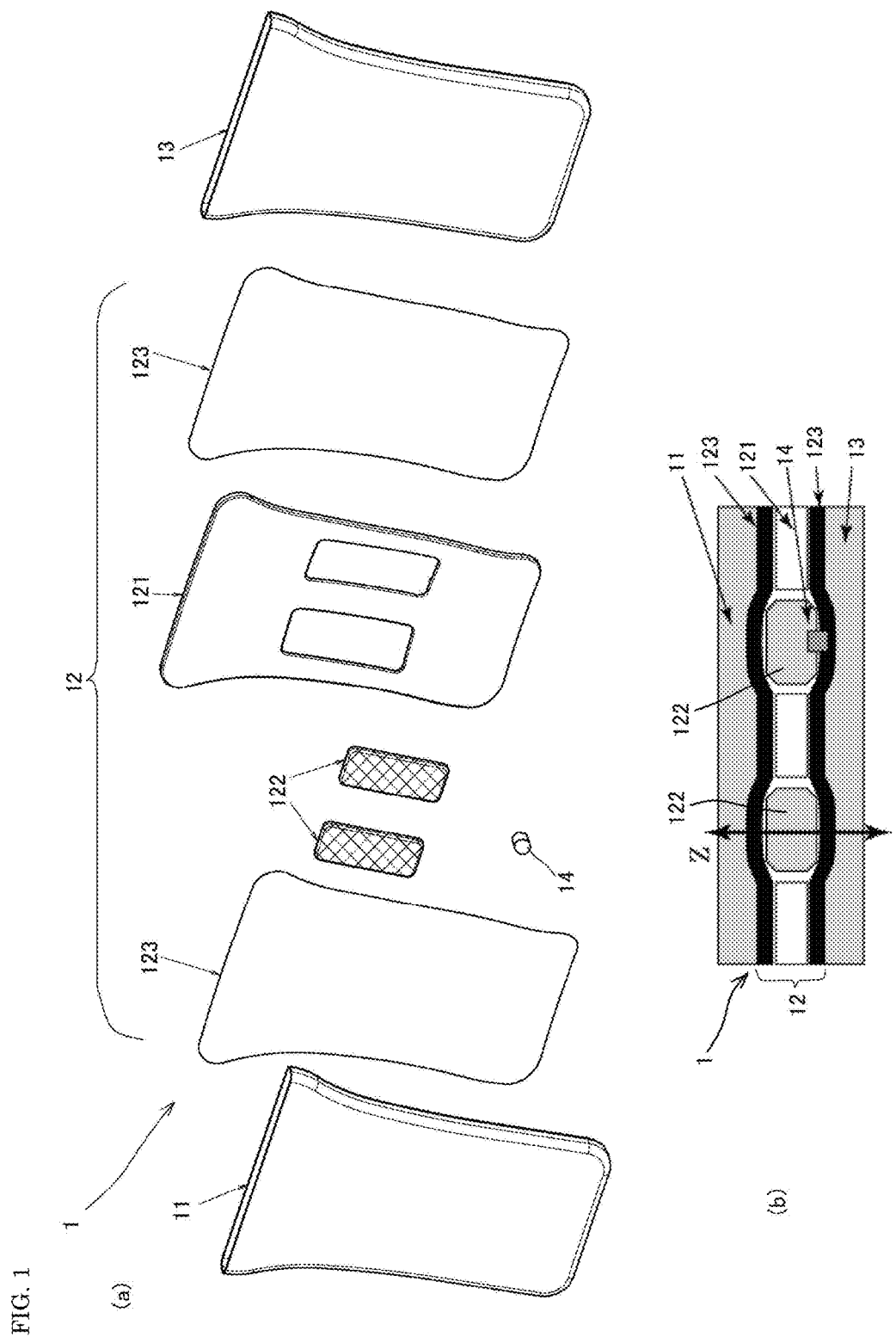
FIG. 1(a) is an exploded view illustrating one example of a biosignal measurement device which is used in one embodiment of the present invention to measure a back body surface pulse wave.
FIG. 1(b) is a sectional view of an essential part thereof.

The present invention will be hereinafter explained in more detail based on embodiments of the present invention illustrated in the drawings. A biosignal collected in the present invention is, for example, finger plethysmogram, electrocardiogram, heart sound, sound and vibration information collected from the back (hereinafter, "back sound and vibration information"), or the like. Incidentally, the back sound and vibration information is the sound and vibration information arising from the motions of the heart and the aorta, which is detected from the back of the upper body of a person, and includes information on the systole and diastole of the ventricles, information on the vascular wall elasticity serving as an auxiliary pump for blood circulation, information on elasticity by blood pressure, and information on reflected waves. Further, a signal waveform accompanying heart rate variability includes information on neural activity of the sympathetic nervous system and the parasympathetic nervous system (information on the parasympathetic nervous system activity including compensation for the sympathetic nervous system), while a signal waveform accompanying aortic oscillation includes information on the sympathetic nerve activity and information on the endocrine system, and thus the back sound and vibration information is suitable for the judgment on the bioregulation function elements from different viewpoints. Accordingly, it is preferred to use the back sound and vibration information as the biosignal.

As a biosignal measurement device for collecting the biosignal, it is possible to use a finger plethysmogram meter, an electrocardiogram, a phonocardiograph, or the like, which is intended to obtain bio-information reflecting the autonomic nervous function other than brain waves. In the case of the back sound and vibration information, it is also possible to use, for example, a pressure sensor, but preferably, a biosignal measurement device 1 used in a drowsy driving warning device (Sleep Buster (registered trademark)) manufactured by Delta Tooling Co., Ltd. is used. FIG. 1 illustrate a schematic structure of the biosignal measurement device 1. The biosignal measurement device 1 can be assembled in a driver seat of a vehicle when used and is capable of collecting biosignals without restraining hands or fingers.

The biosignal measurement device 1 which collects the back sound and vibration information will be briefly explained. As illustrated in FIGS. 1(a), (b), the biosignal measurement device 1 has a three-layer structure in which a first layer 11, a second layer 12, and a third layer 13 are stacked in the order mentioned from the top, and when it is used, the first layer 11 formed of a three-dimensional knitted fabric or the like is located on a human body side being a biosignal detection target. Therefore, a biosignal from the back of the trunk of the human body, in particular, sound and vibration information (back body surface pulse wave (including APW)) of the cardiovascular system including biosound generated in accordance with the vibration of the ventricles, the atrium, and great vessels (direct sound from the trunk or a bioacoustic signal) is propagated first to the first layer 11 being a biosignal input system. The second layer 12 functions as a resonance layer which emphasizes the biosignal, in particular, the sound and vibration of the cardiovascular system propagated from the first layer 11, by means of a resonance phenomenon or a beat phenomenon, and includes a casing 121 formed of a bead foam, three-dimensional knitted fabrics 122 functioning as natural oscillators, and a film 123 generating membrane vibration. In the second layer 12, a microphone sensor 14 is disposed to detect the sound and vibration information. The third layer 13 is stacked opposite the first layer 11 with the second layer 12 therebetween and reduces external sound and vibration input.

Figure 2:
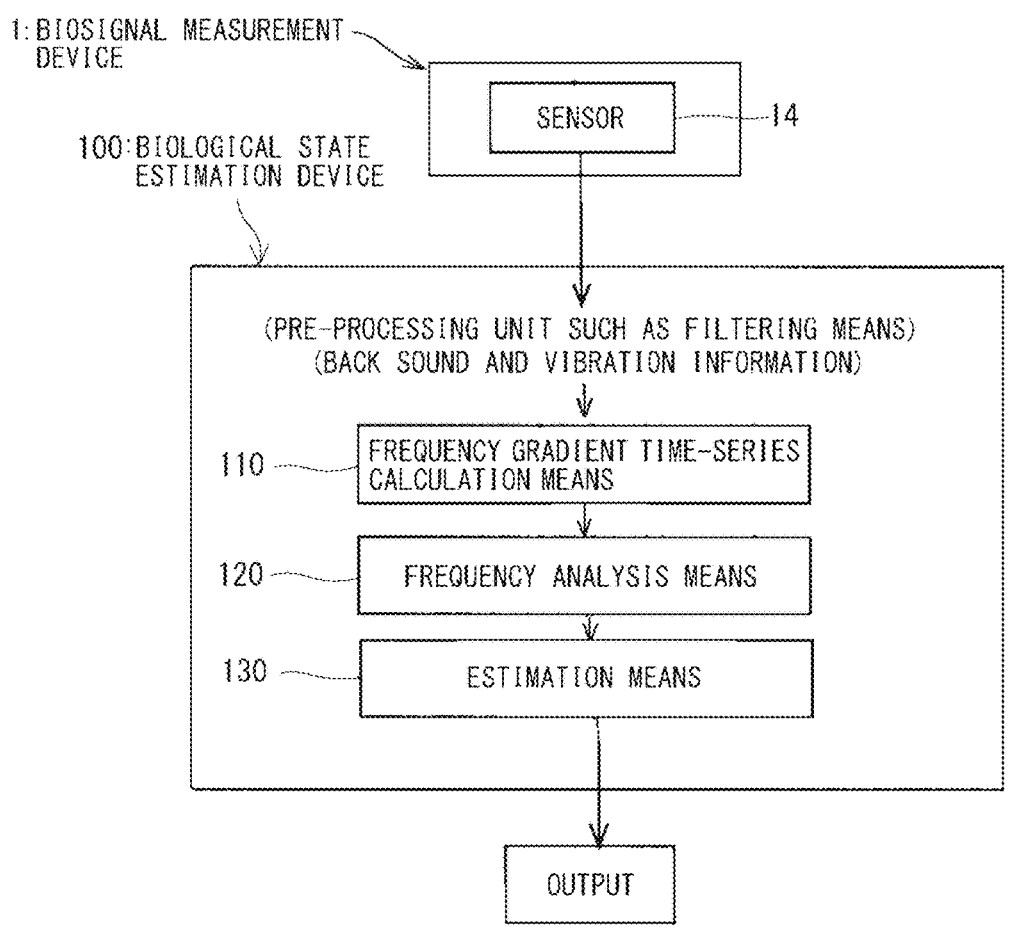
FIG. 2 is a diagram schematically illustrating a configuration of a biological state estimation device according to one embodiment of the present invention.

Next, there will be explained a configuration of a biological state estimation device 100 of this embodiment based on FIG. 2. The biological state estimation device 100 is constituted by a computer (including a microcomputer or the like), and in its storage, a computer program causing the computer to function as a frequency gradient time-series waveform calculation means 110, a frequency analysis means 120, and an estimation means 130 is set. Thereby, the computer executes a frequency gradient time-series waveform calculation procedure, a frequency analysis procedure, and an estimation procedure which are a biological state estimation procedure. In the biological state estimation means 100, the frequency gradient time-series waveform calculation means 110, the frequency analysis means 120, and the estimation means 130 can also be constituted as a frequency gradient time-series waveform calculation circuit, a frequency analysis circuit, and an estimation circuit which are electronic circuits caused to operate in predetermined procedures by the above-described computer program. It goes without saying that, in the following explanation, structures named with "means" other than the biological state estimation means 100, the frequency gradient time-series waveform calculation means 110, the frequency analysis means 120, and the estimation means 130 can also be constituted as electronic circuit components.

Incidentally, the computer program may be stored in a computer-readable recording medium. By using the recording medium, it is possible to, for example, install the above-described program in the above-described computer. Here, the recording medium in which the above-described program is stored may be a non-transitory recording medium. The non-transitory recording medium is not limited in particular, and examples thereof include recording mediums such as a flexible disk, a hard disk, CD-ROM, MO (magneto-optical disk), DVD-ROM, and a memory card. Further, it is also possible to install the above-described program by transmitting it to the above-described computer via communication lines.

Figure 3:
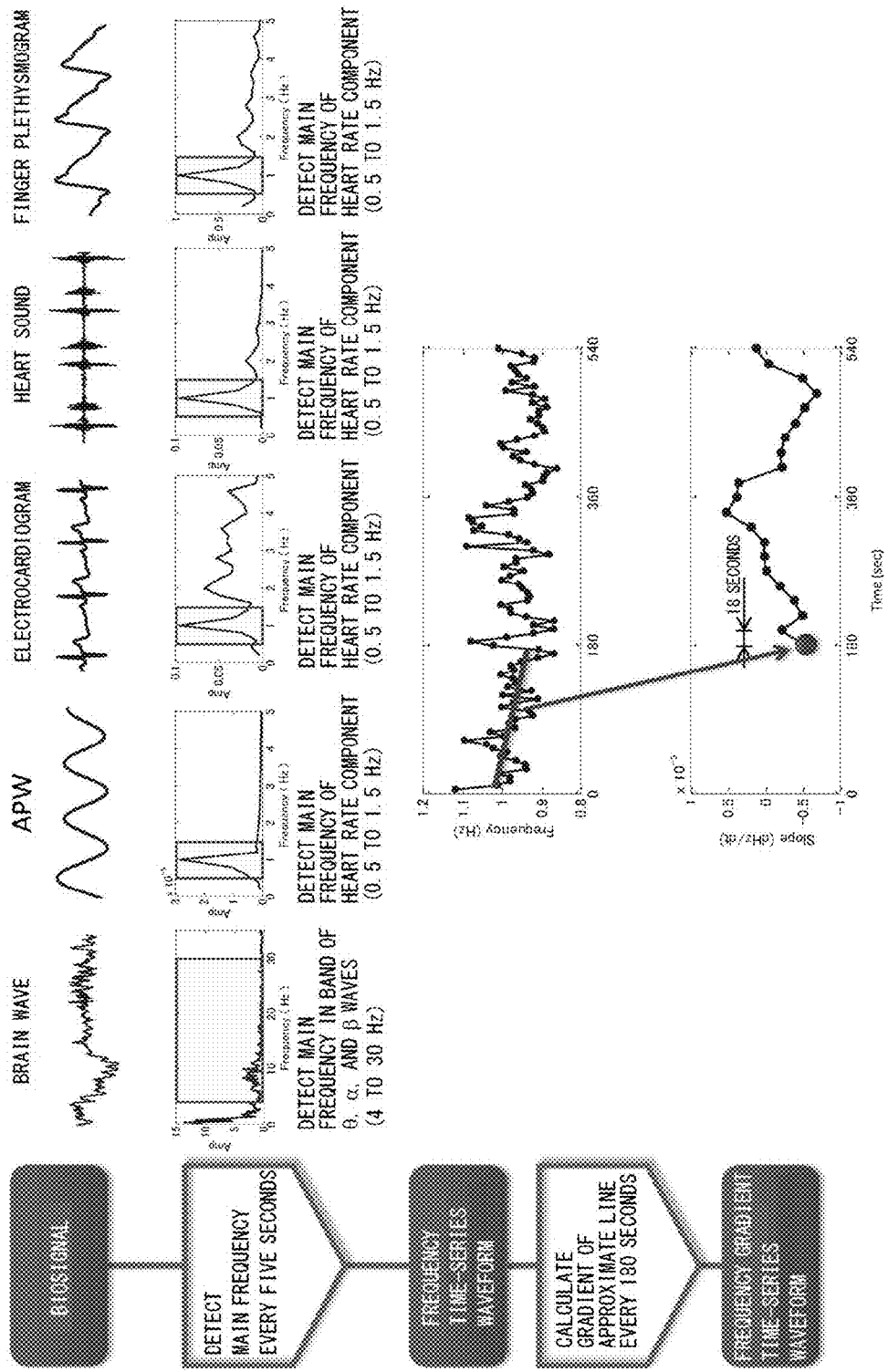
FIG. 3 is a diagram for explaining a calculating method of a frequency gradient time-series waveform calculation means.

The frequency gradient time-series waveform calculation means 110 extracts, every five seconds, main frequencies from time-series waveforms of biosignals highly correlated with the autonomic nervous function being an analysis target, for example, a back body surface pulse wave (APW) of around 1 Hz resulting from filtering of the back sound and vibration information obtained from the sensor 14 of the above-described biosignal measurement device 1, a finger plethysmogram obtained from a finger plethysmogram meter, an electrocardiogram obtained from an electrocardiograph, and a heart sound obtained from a phonocardiograph and obtains time-series waveforms of the frequencies and thereafter obtains frequency gradient time-series waveforms (refer to FIG. 3) by slide calculation of the time-series waveforms of the frequencies. As the frequency gradient time-series waveform calculation means 110, there are the following two methods as disclosed in Patent Documents 1 and so on described above by the present inventors: a method (zero-cross method) using switching points from positive to negative (zero-cross points) in the time-series waveform of each of the biosignals; and a method (peak detection method) performing smoothing differentiation of the time-series waveform of the back body surface pulse wave (APW) to obtain the time-series waveform using peak values (peak points).

In the zero-cross method, after the zero-cross points are obtained, they are divided in, for example, five-second segments, and a reciprocal of a time interval between the zero-cross points of the time-series waveform included in each five-second period is obtained as an individual frequency f, and an average value of the individual frequencies f in the five-second period is adopted as a value of a frequency F in the five-second period (main frequency). Then, the frequencies F obtained every five seconds are plotted in a time-series manner, and thereby the time-series waveform of variation of the frequency is obtained.

In the peak detection method, the above-described time-series waveform of each of the biosignals is subjected to a smoothing differentiation method by, for example, Savitzky and Golath, and thereby the peak values are obtained. Next, the peak values are divided in, for example, five-second segments, a reciprocal of a time interval between the peak values of the time-series waveform included in the five-second period is obtained as an individual frequency f, and an average value of the individual frequencies f in the five-second period is adopted as a value of a frequency F in the five-second period. Then, the frequencies F obtained every five seconds are plotted in a time-series manner, and thereby the time-series waveform of variation of the frequency is obtained.

In the time-series waveform of the variation of the frequency obtained by the zero-cross method or the peak detection method, the frequency gradient time-series waveform calculation means 110 sets time windows each with a predetermined time width (for example, 180 seconds) overlapping with each other by a predetermined time (for example, 18 seconds), and obtains a gradient of the frequency in each of the time windows by a least square method to obtain the time-series waveform of the gradient. This slide calculation is repeated in sequence, and the time-series variation of the gradient of the frequency of the biosignal is output as the frequency gradient time-series waveform.

The above-described back body surface pulse wave (APW) out of the biosignals is a biosignal mainly including the state of control of the heart which is the central nervous system, that is, it is a biosignal including information on the state of sympathetic innervation of arteries and information on the manifestation of the sympathetic nervous system and the parasympathetic nervous system. The frequency gradient time-series waveform obtained by the zero-cross method is more correlated with the state of the control of the heart and reflects the manifestation state of the sympathetic nervous system, while the frequency gradient time-series waveform obtained by the peak detection method is more correlated with the heart rate variability. Therefore, in order to more clearly grasp the state of the autonomic nervous function, it is preferred to use the frequency gradient time-series waveform obtained by the zero-cross method.

Incidentally, the reason for using the frequency gradient time-series waveform as the basis of an index to grasp a biological state is based on the following findings found by the present inventor. That is, it has been known that a sleep pattern is affected by a circadian rhythm, homeostasis, a biological clock, or the like. The sleep-wake rhythm is controlled by an oscillator of the biological clock, and is controlled also by the homeostasis to eliminate fatigue to return to an original state. The interaction between the oscillator to beat the same rhythm and the homeostasis, what is called, fighting each other appears as heart rate variability or breathing and body temperature variability. Then, in order to keep the heartbeat or breathing to a certain state, low-frequency fluctuation works rather than the heart rate or the breathing rate. Further, the ease of sleep induction is affected by a decrease in body temperature of a deep region and secretion of melatonin. The decrease in body temperature of the deep region leads to an increase in skin temperature, and further leads to cutaneous vasodilatation, and the cutaneous vasodilatation causes an increase in cutaneous blood flow and heat transfer from the deep region of a body to the body surface occurs. That is, the decrease in body temperature of the deep region, the increases in skin temperature and cutaneous blood flow, and the cutaneous vasodilatation accompanying them cause a decrease in sympathetic nerve function. These various phenomena indicate that the decrease in sympathetic nerve function occurs at a sleep transition time. Further, body temperature regulation activity is included in a VLF region with a very low frequency component of 0.0033 to 0.04 Hz.

These various phenomena to occur in the heart and the vascular system are caused due to fluctuation controlling a fluid, and the fluctuation is included in frequencies, amplitudes, and base lines. Thus, the frequency gradient time-series waveform which detects a component of this fluctuation, which is found out by the present inventor, is applied also to the present invention. Normally, in order to obtain the component of the VLF band by an FFT analysis, data for 24 to 48 hours are required. It is difficult to perform a real-time analysis naturally. However, the method of obtaining the frequency gradient time-series waveform makes it possible to obtain time-series waveforms of fluctuations of parameters of the frequency, the amplitude, and the base line, that is, the time-series waveforms are obtained by obtaining how the fluid varies from differential values of the parameters and detecting their singular points, and thus, it is possible to grasp how the fluid fluctuates by a change in fluid energy per unit time.

The frequency analysis means 120 is a means which frequency-analyzes the frequency gradient time-series waveform obtained from the frequency gradient time-series waveform calculation means 110 every predetermined time range to obtain a power spectrum. As a result of the frequency analysis, this embodiment is constituted that the relationship between frequency and power spectrum density is output in a log-log graph or in a linear graph.

The estimation means 130 is a means which estimates a time-series variation of the biological state which is specified by a brain wave state and brain waves by means of a time-series variation of an analyzed waveform (fluctuation waveform) being the output result of the frequency analysis obtained by the frequency analysis means 120. Concretely, in the storage of the computer constituting the biological state estimation procedure 100, there are stored beforehand corresponding data resulting from making the analyzed waveform (fluctuation waveform), which is the output result of the frequency analysis, correspond to an output result of brain waves measured by an electroencephalograph. The estimation means 130 compares the output result of the frequency analysis result when obtained by the frequency analysis means 120 with the corresponding data stored in the storage. This makes it possible to estimate a brain wave state and a biological state corresponding to the brain wave state.

The "brain wave state" indicates an output result of brain waves itself, for example, which one of the α wave, the β wave, and the θ wave is in a predominant state in the brain wave distribution ratios, or the like, and the "biological state corresponding to the brain wave state" is biological states to be judged by brain waves: for example, the case where the distribution ratio of α wave is 50% or more is a "wakeful state;" the case where the θ wave is predominant over the α wave, the θ wave is 20% or more, and the α wave is 40% or less, and preferably, the β wave is 40% or less in addition is a "sleep state;" and the case where the α wave or the β wave is 40% or less, the θ wave is 20% or less, the distribution ratio of α wave is the same as or predominant over the distribution ratio of θ wave when compared, and the distribution ratio of β wave is the same as or predominant over the distribution ratio of θ wave when compared is a "state of sleepiness strongly resisting while being in a wakeful state."

In the meantime, the frequency analysis means 120, as described above, outputs the result of the frequency analysis in a log-log graph or in a linear graph with the relationship between frequency and power spectrum density, and as the corresponding data, in the case of the result of the frequency analysis being output in a log-log graph, for example, a correspondence between a brain wave state and a biological state corresponding to the brain wave state and an approximate line of an analyzed waveform (fluctuation waveform) of the result is preferably set beforehand to be stored in the storage.

Concretely, the case where the approximate line is relatively approximate to 1/f is estimated as a "sleep state where the θ wave is predominant over the α wave and the θ wave is equal to or more than predetermined values and the α wave is equal to or less than predetermined values." The case where the approximate line is relatively approximate to $1/f^2$ is made to correspond so as to be estimated as a "state of sleepiness strongly resisting while being in a wakeful state" where the α wave or the β wave is the same as or predominant over the θ wave and the distribution ratio of β wave is the same as or predominant over the distribution ratio of θ wave when compared. Further, in the case of a "wakeful and relaxed state" where the α wave is equal to or more than predetermined values and the θ wave is equal to or less than predetermined values in the brain wave distribution ratios, the approximate line exhibits, if anything, a tendency of being approximate to 1/f, but the approximate line often exhibits a gradient between the above-described "sleep state" and "state of sleepiness strongly resisting while being in a wakeful state." Incidentally, numerical values of the distribution ratios of α wave, β wave, and θ wave are made to correspond to the numerical values explained as an example in the above-described "brain wave states."

Thereby, the estimation means 130 obtains the analyzed waveform (fluctuation waveform), which is the output result of the frequency analysis, thereby being able to refer to its corresponding data and estimate a brain wave state and a biological state corresponding to the brain wave state to output the result. Incidentally, whether or not the approximate line is approximate to 1/f is set whether the gradient is in a range of −0.8 to −2, for example, and whether or not the approximate line is approximate to $1/f^2$ is set whether the gradient is in a range of about −2 to −3.5. The estimation means 130 judges this gradient and estimates the brain wave state according to whether the gradient is contained in any one of ranges. However, due to individual difference, setting of the numerical value of the gradient may be performed every individual.

In this manner, it is only necessary for the estimation means 130 to obtain the analyzed waveform (fluctuation waveform), which is the output result of the frequency analysis, and compare the gradient of its approximate line with the correlation data stored in the storage beforehand to then estimate the brain wave state and the biological state corresponding to the brain wave state, and thus the estimation is easy, and at an estimation time, it is possible to cause the computer to execute rapid calculation processing without having a large calculation load on the computer.

In the case where the result of the frequency analysis obtained by the frequency analysis means 120 is output in a linear graph representing the relationship between frequency and power spectrum density, corresponding data resulting from making variations in the linear graph correspond to the "sleep state," the "state of sleepiness strongly resisting while being in a wakeful state," and the "wakeful state" in the above-described brain wave judgments are created to be stored beforehand. The variations in the linear graph are preferably grasped by the way how the frequency at the maximum peak of the power spectrum density (to be referred to as a "predominant frequency" in this application) appears. As the way how the frequency appears, it is possible to cite, for example, the position of the predominant frequency and the magnitude of the power spectrum density of the predominant frequency. In this case as well, by narrowing down to the way how the predominant frequency appears, the estimation means 130 does not put a large load on the calculation processing of the computer.

Experimental Example 1

(Experiment Method)

In a supine position, a 60-minute sleep-inducing experiment from wakefulness to sleep was performed. An experiment time ranges from 2 p.m. to 5 p.m. Subjects are healthy 21 males (27.9±2.4 years of age). Measurement items are brain waves, APW, an electrocardiogram, hear sounds, and a finger plethysmogram. In order to detect the wakeful state and the sleep state, for 30 minutes after the experiment started, the subjects were obliged to maintain the wakeful state, and thereafter, this obligation was released and whether the wakeful state or the sleep state was left to the free will of each of the subjects.

(Experimental Result)

Figure 4:
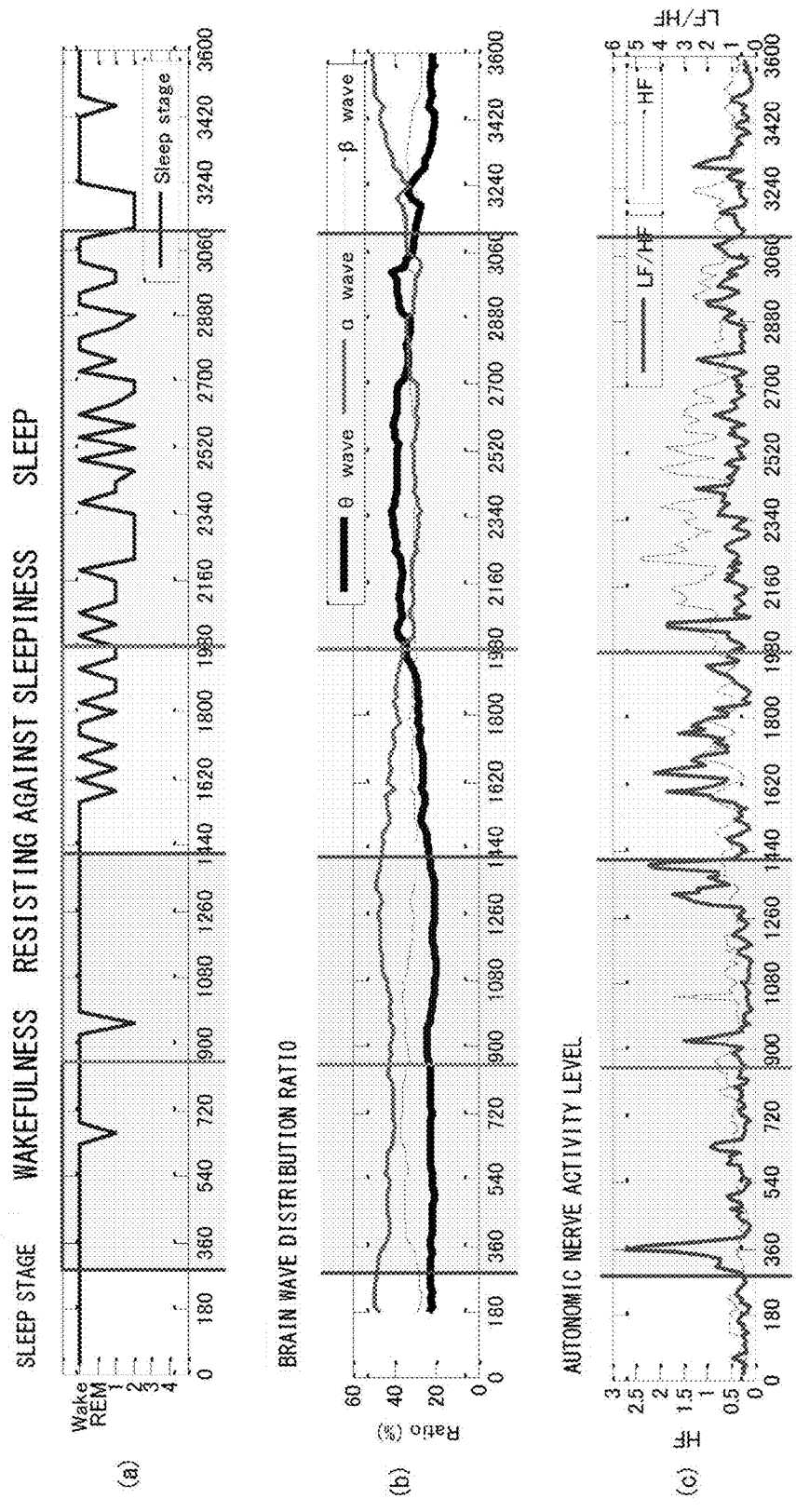
FIGS. 4(a) to (c) are data of a subject A in an experimental example 1.
Figure 5:
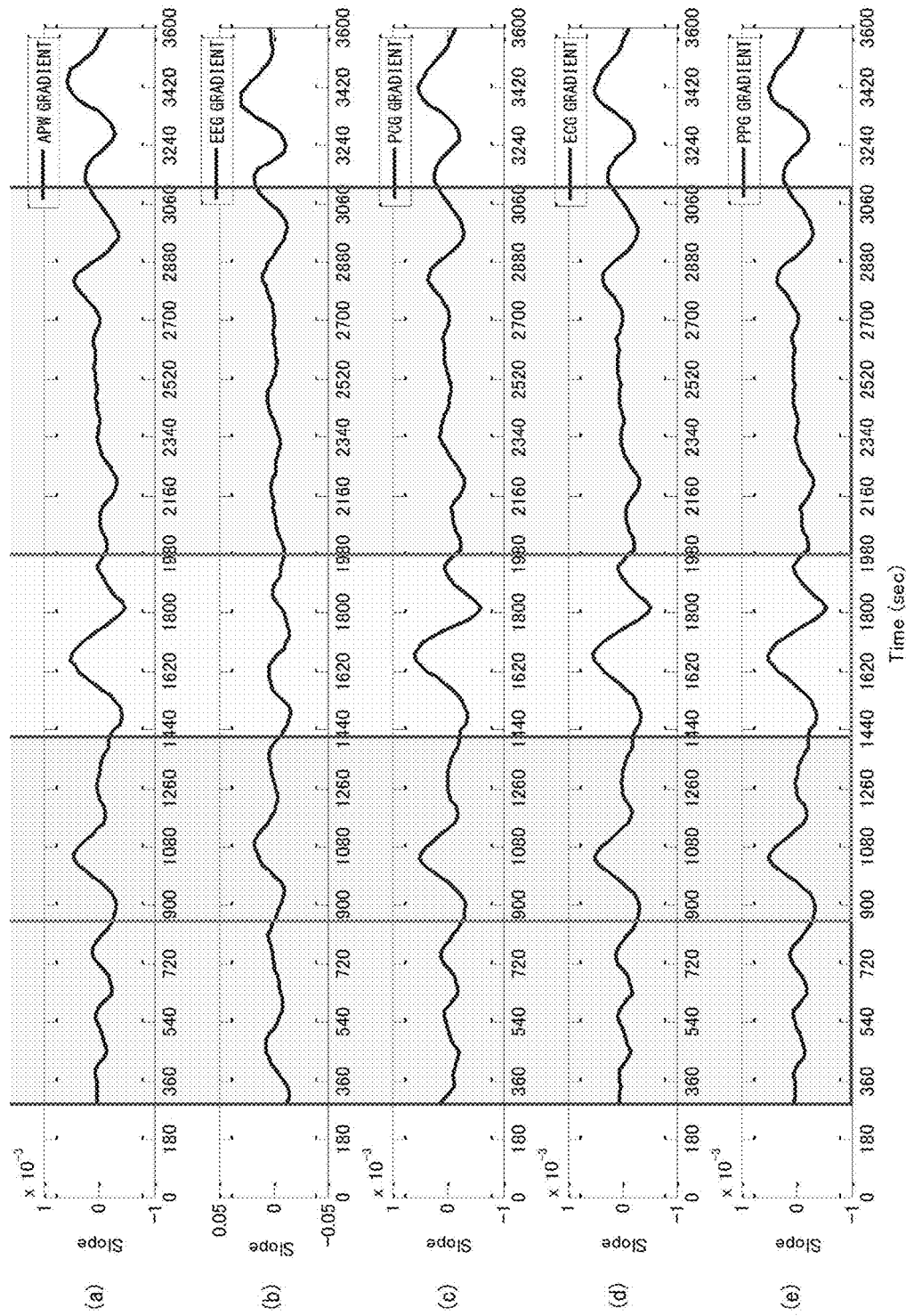
FIGS. 5(a) to (e) illustrate frequency gradient time-series waveforms of biosignals.
Figure 6:
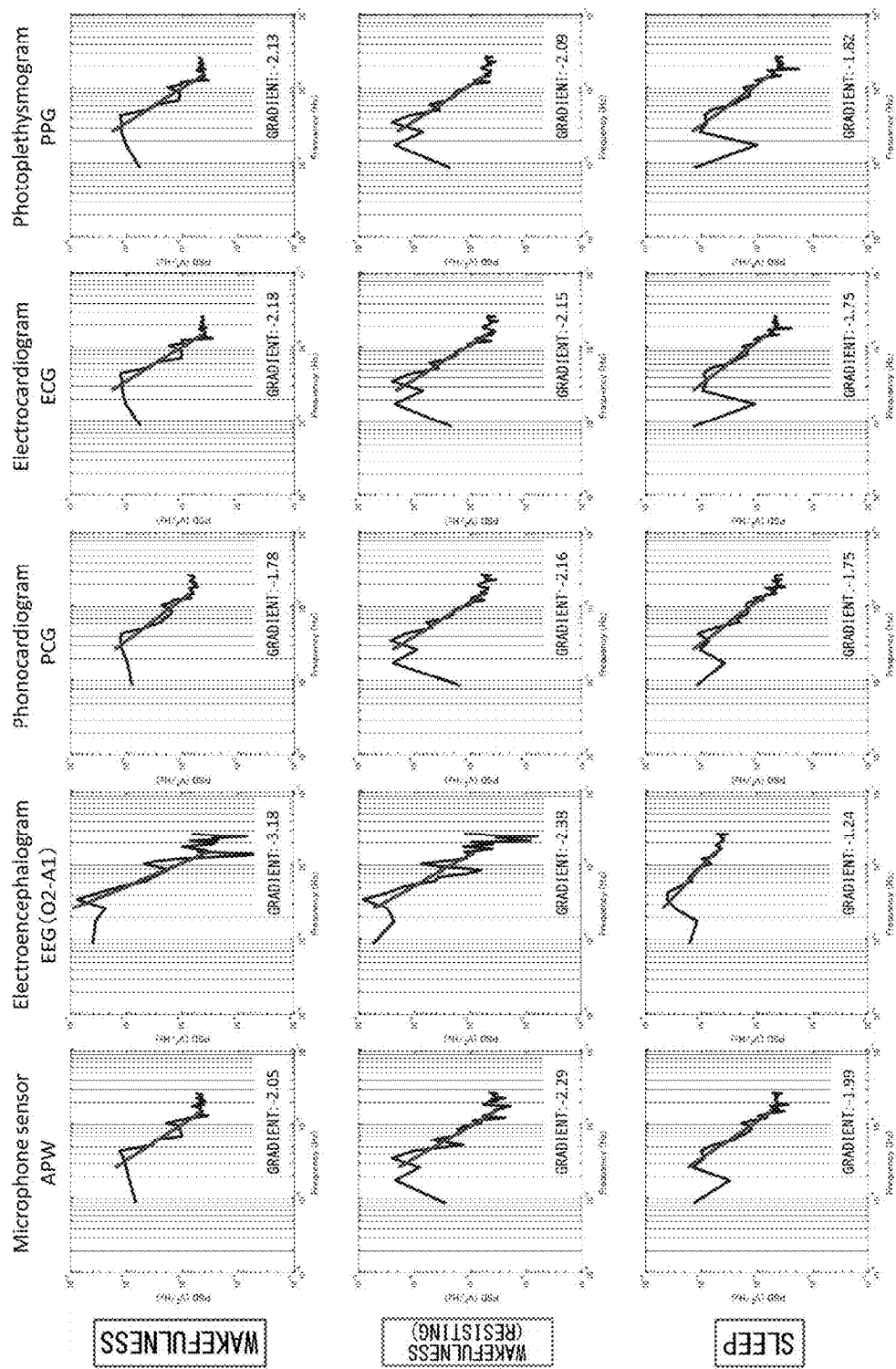
FIG. 6 is charts illustrating analyzed waveforms of analysis results of the respective gradient time-series waveforms in FIGS. 5(a) to (e) each being output in a log-log graph and their approximate lines.
Figure 7:
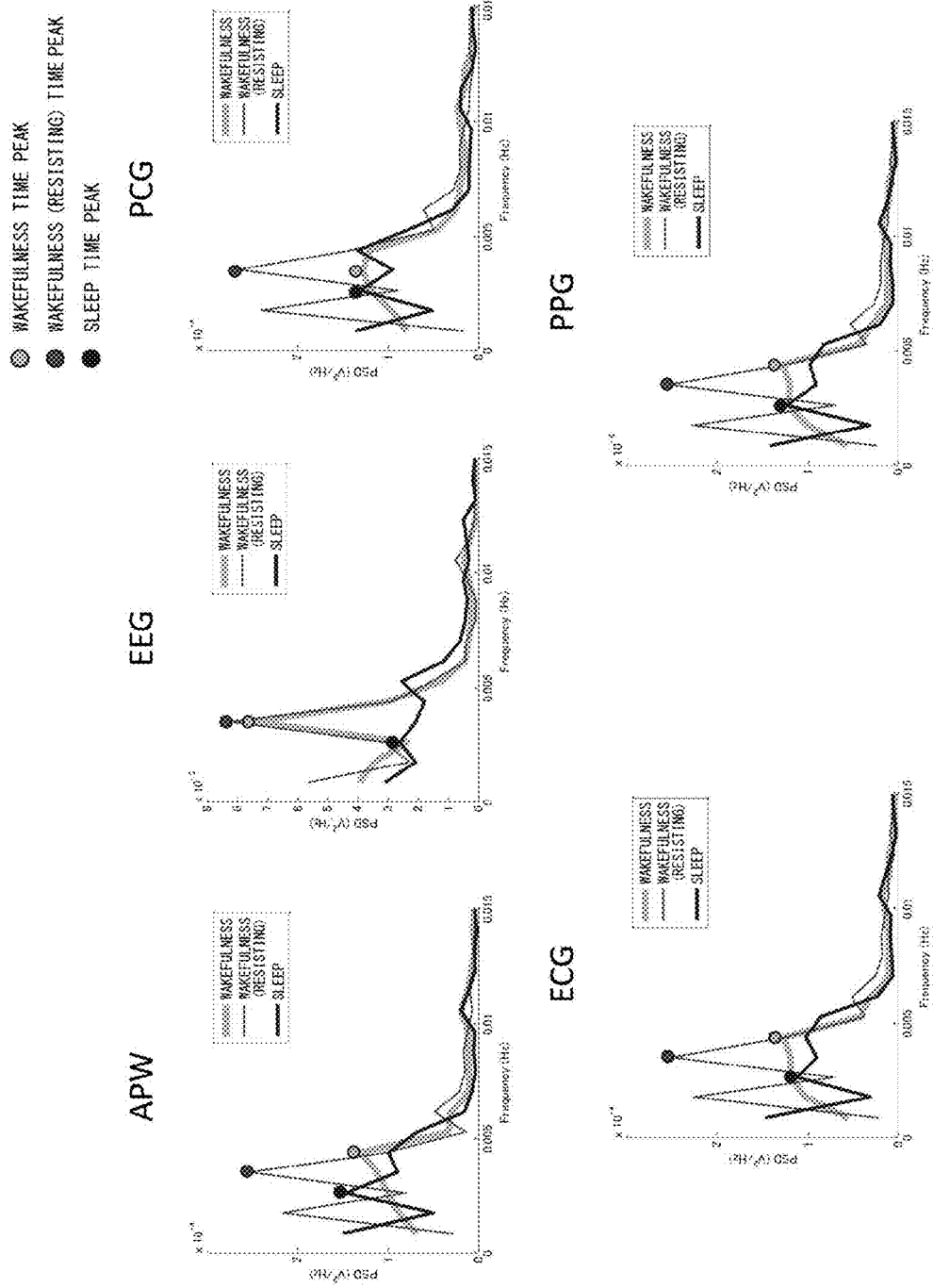
FIG. 7 is charts illustrating analyzed waveforms of the analysis results of the respective gradient time-series waveforms in FIGS. 5(a) to (e) each being output in a linear graph and their predominant frequencies.

FIGS. 4(*a*) to (*c*) to FIG. 7 illustrate experimental results of a subject A. FIGS. 4(*a*) to (*c*) illustrate a sleep stage, brain wave distribution ratios (distribution ratios of α wave, β wave, and θ wave), and activity levels of the sympathetic nerve (LF/HF) and the parasympathetic nerve (HF) which are calculated from an electrocardiogram, and these results reveal that the subject A maintains a high level wakeful state with no sleepiness until around 900 seconds and thereafter maintains a state of resisting against sleepiness while being in a wakeful state (sleepiness resisting state (wakefulness (resisting)) until around 2000 seconds, and then shifts to sleep. FIGS. 5(*a*) to (*e*) illustrate frequency gradient time-series waveforms of a back body surface pulse wave (APW), a brain wave (EEG), a heart sound (PCG), an electrocardiogram (ECG), and a finger plethysmogram (PPG) which are obtained by the frequency gradient time-series waveform calculation means 110. The frequency analysis means 120 frequency-analyzed the respective frequency gradient time-series waveforms in FIGS. 5(*a*) to (*e*) in a time period of the wakeful state, a time period of resisting against sleepiness, and a time period of the sleep state and obtained the relationship between the frequency and the power spectrum density of each of the biosignals. FIG. 6 illustrates analyzed waveforms of the analysis results each being output in a log-log graph and their approximate lines, and FIG. 7 illustrates analyzed waveforms of the analysis results each being output in a linear graph and their predominant frequencies.

FIG. 6 reveals that in the "sleep state," the gradient of the approximate line of the brain wave is −1.24, and the gradients of the approximate lines of the other biosignals are in a range of −1.75 to −1.99. Thereby, corresponding data resulting from making the gradients in a range of −0.8 to −2, as the gradient approximate to 1/f, correspond to the "sleep state" judged by the brain wave are set beforehand, and thereby the estimation means 130 can estimate the same state as the "sleep state," which is estimated from the brain wave, by the gradients of the approximate lines of the biosignals other than the brain wave.

In the "sleepiness resisting state (wakefulness (resisting)," the gradient of the approximate line of the brain wave is −2.38 to indicate the gradient approximate to $1/f^2$ in a range of −2 to −3.5. The gradients of the approximate lines of the other biosignals are also in a range of −2.09 to −2.29, and thereby the estimation means 130 can judge the "sleepiness resisting state" in the same manner as the brain wave.

In the "wakeful state with no sleepiness," the gradient of the approximate line of the brain wave is −3.18, which is the gradient approximate to $1/f^2$. The gradients of the approximate lines of the other biosignals other than PCG are also the gradient approximate to $1/f^2$. As is clear from FIGS. 4(*a*) to (*c*), in the "wakeful state" until about 900 seconds, the sympathetic nerve activity is predominant, which is not in a relaxed state, and thus it is thought that the gradient which can be judged to be approximate to $1/f^2$ has been output.

In the case of the subject A, only the approximate lines of the analyzed waveforms in the log-log graph make it possible to clearly distinguish the "sleep state" from the "sleepiness resisting state" or the "wakeful state" as above to estimate the biological state. However, distinguishing between the "sleepiness resisting state" and the "wakeful state is not clear. Therefore, in such a case, the analyzed waveforms in the linear graph in FIG. 7 are preferably used in combination.

When FIG. 7 is seen, as for the position of the predominant frequency, the predominant frequency appears around 0.005 Hz in the "sleepiness resisting state" and the "wakeful state," and appears around 0.0025 Hz in the "sleep state." Therefore, this predominant frequency difference enables the estimation means 130 to distinguish the "sleep state" from the "sleepiness resisting state" or the "wakeful state" and estimate the biological state similarly to the case of using the above-described log-log graphs in FIG. 6. Further, the "(wakeful and) sleepiness resisting state" and the "wakeful state" can be distinguished by the magnitude of the power spectrum density. In terms of all the biosignals including the brain wave, the power spectrum density is rather larger in the "sleep resisting state." Therefore, the magnitude differences in the power spectrum density are stored beforehand as the corresponding data, thereby enabling the estimation means 130 to distinguish the "sleepiness resisting state" and the "wakeful state" and estimate the biological state.

Figure 8:
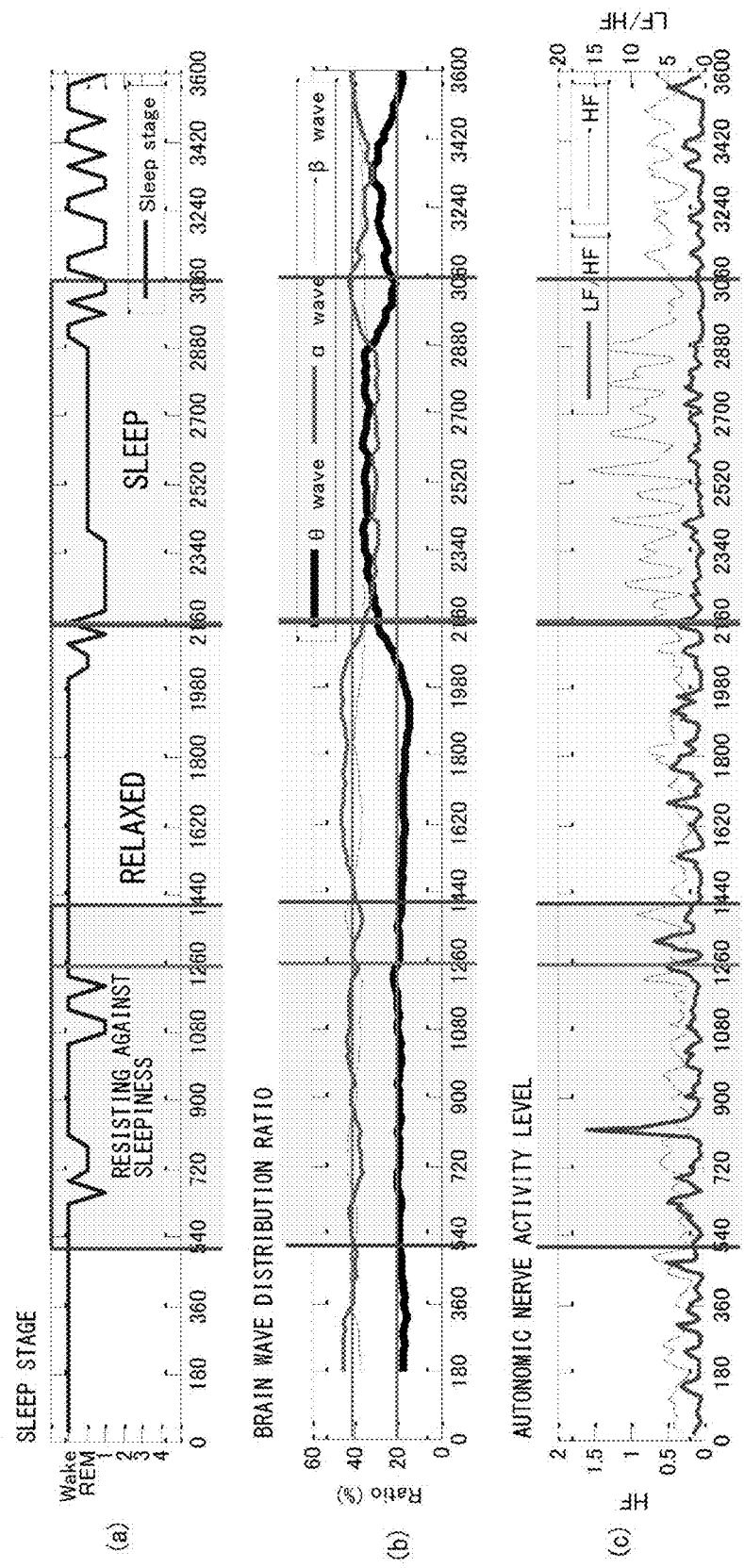
FIGS. 8(a) to (c) are data of a subject B in the experimental example 1.
Figure 9:
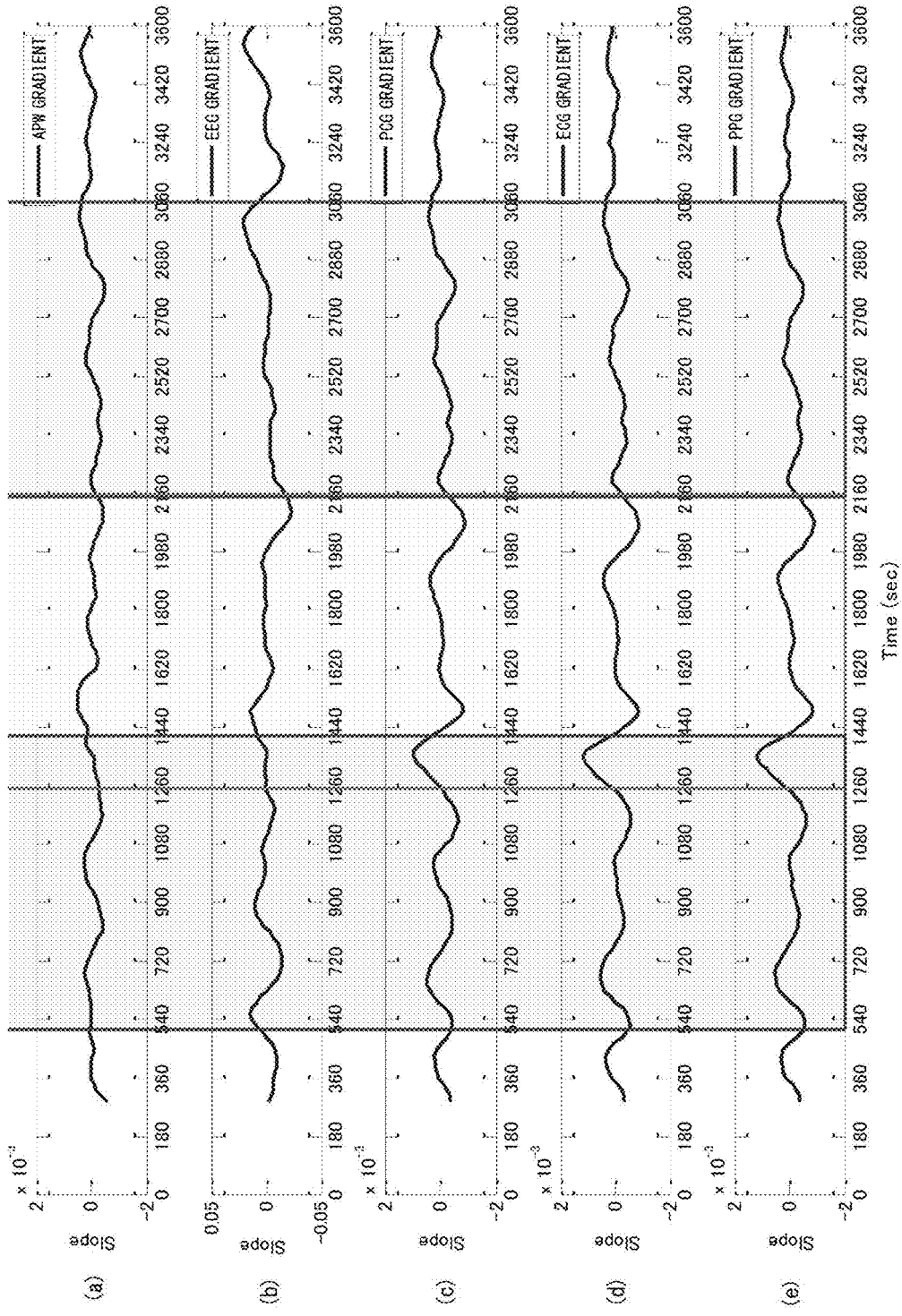
FIGS. 9(a) to (e) illustrate frequency gradient time-series waveforms of biosignals.
Figure 11:
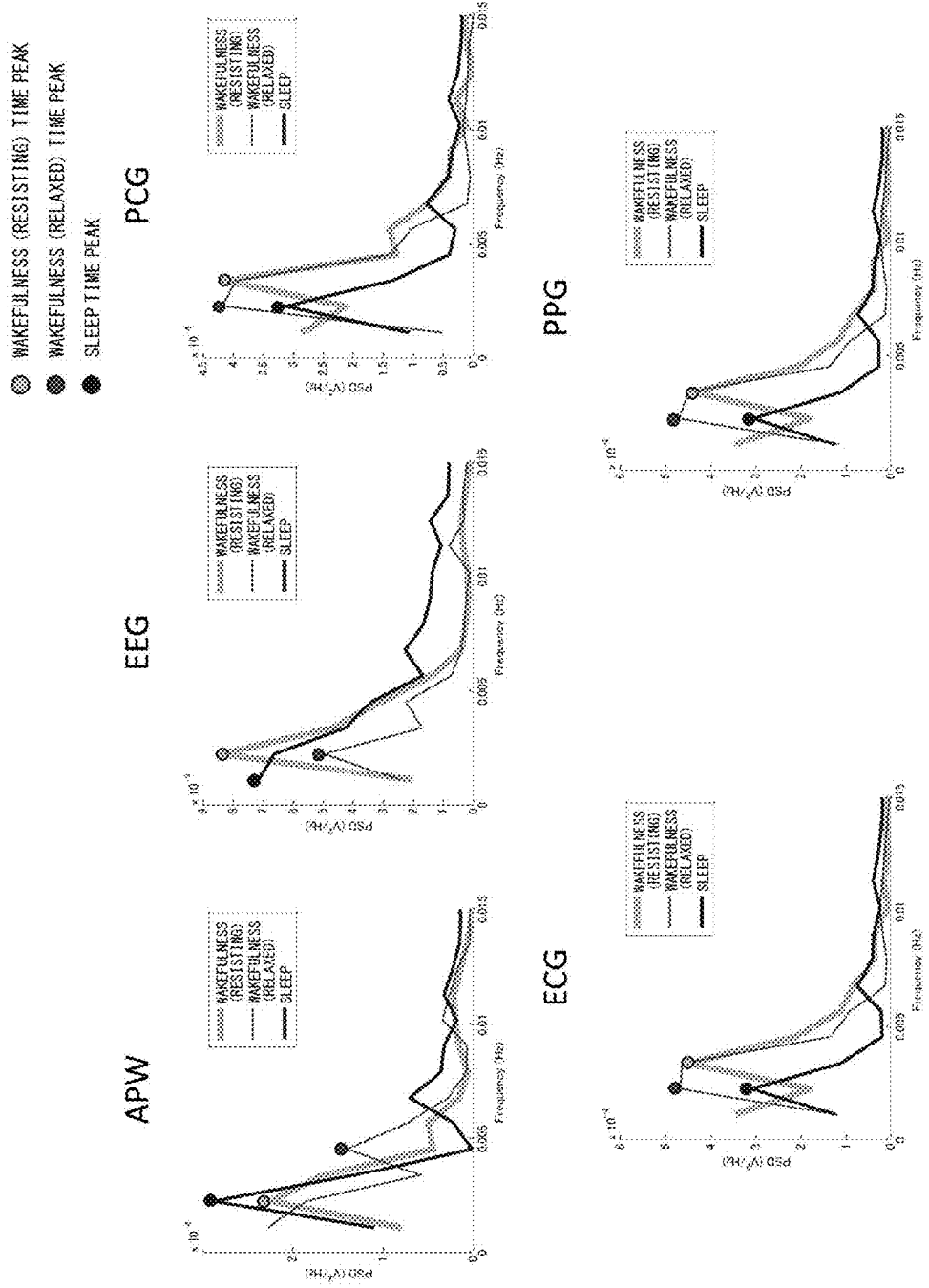
FIG. 11 is charts illustrating analyzed waveforms of the analysis results of the respective gradient time-series waveforms in FIGS. 9(a) to (e) each being output in a linear graph and their predominant frequencies.

FIGS. 8(*a*) to (*c*) to FIG. 11 are experimental results of a subject B. FIGS. 8(*a*) to (*c*) reveal that the subject B is in a state of resisting against sleepiness while being in a wakeful state (sleepiness resisting state (wakefulness (resisting)) until around 1300 seconds since around 500 seconds, maintains a relaxed wakeful state where HF indicating the parasympathetic nerve activity is predominant until around 2200 seconds since 1400 seconds, and then shifts to sleep since around 2200 seconds.

Figure 10:
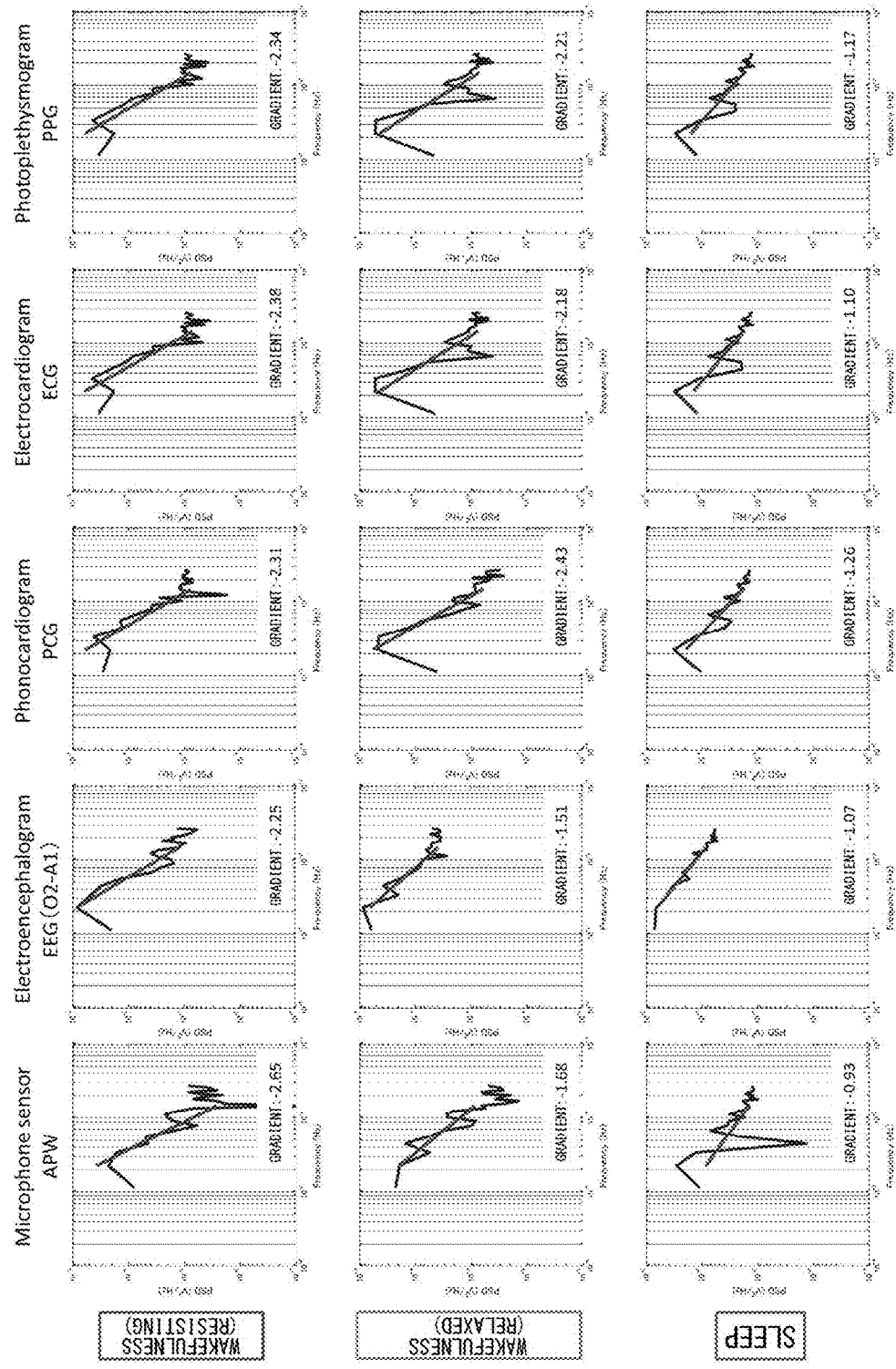
FIG. 10 is charts illustrating analyzed waveforms of analysis results of the respective gradient time-series waveforms in FIGS. 9(a) to (e) each being output in a log-log graph and their approximate lines.

When gradients of approximate lines in FIG. 10 are seen, in the "sleep state," the gradient of the approximate line of the brain wave is −1.07 and the gradients of the approximate lines of the other biosignals are in a range of −0.93 to −1.26, which can be said that the gradients are approximate to 1/f. In the "sleepiness resisting state (wakefulness (resisting))," the gradient of the approximate line of the brain wave is −2.25 and the gradients of the approximate lines of the other biosignals are also in a range of −2.31 to −2.65, which are approximate to $1/f^2$. This enables the estimation means 130 to judge the "sleepiness resisting state."

In the "(relaxed) wakeful state," the gradient of the approximate line of the brain wave is −1.51 and the gradient of the approximate line of APW is −1.68, which is approximate to this. Therefore, when APW is used, its gradient is judged to be the gradient approximate to 1/f similarly to the brain wave. However, the gradients of the other indexes are −2.18 to −2.43 to be approximate to $1/f^2$.

In the meantime, when seen in the linear graphs in FIG. 11, in the "sleep state," the predominant frequency appears around 0.0025 Hz in each of the cases. In the "(relaxed) wakeful state," the predominant frequency appears around 0.0025 Hz in the indexes other than APW. In the case of the "sleepiness resisting state," the predominant frequency appears around 0.005 Hz in the indexes other than APW. Therefore, the predominant frequency appears around 0.0025 Hz in many of the indexes in the "sleep state" and the "(relaxed) wakeful state," while the predominant frequency appears around 0.005 Hz in many of the indexes in the "sleep resisting state."

In order to increase the accuracy of estimation by the estimation means 130, it is preferred to judge the biological state by using the log-log graph and the linear graph in combination and estimate the biological state by using estimated results of the plural biosignals (APW, electrocardiogram, heart sound, and finger plethysmogram) in combination.

As above, it is found out by referring to FIG. 6 and FIG. 7 or FIG. 10 and FIG. 11 that the estimation means 130 only uses the other biosignals relating to the autonomic nerve to obtain their time-series variations without measuring brain waves, thereby being able to estimate time-series variations of a brain wave state and a biological state corresponding to the brain wave state. It is possible to easily grasp the time-series variation, that is, a shift from the "wakeful state" to the "sleep state" through the "state of resisting against sleepiness while being in a wakeful state," for example, in place of brain waves.

Next, by using the above-described predominant frequencies obtained from the frequency gradient time-series waveforms, correlations each between a difference between rhythm of the biosignal in the sleep state and rhythm of the biosignal in the sleepiness resisting state (periodic variation value (Pv (Hz)) and judged results of the brain wave were compared.

The periodic variation value (Pv (Hz)) was obtained by the following expression.

$$Pv = Dfw - Dfs$$

Incidentally, Dfw (Hz) is the predominant frequency in the "sleepiness resisting state (wakeful state)" and Dfs (Hz) is the predominant frequency in the "sleep state."

Data of target subjects, which were used for the comparison, are data of the 16 subjects who fell asleep out of the 21 subjects in total. Comparison results are illustrated in Tables 1 to 5 according to APW, the brain wave, the heart sound, the electrocardiogram, and the finger plethysmogram.

TABLE 1

| | | Periodic variation value (unit: person) | |
|---|---|---|---|
| Rhythm of APW | | + | − |
| Brain wave judgment | + | 7 | 3 |
| | − | 0 | 6 |

Significance probability p = 0.011

TABLE 2

| | | Periodic variation value (unit: person) | |
|---|---|---|---|
| Rhythm of brain wave | | + | − |
| Brain wave judgment | + | 9 | 1 |
| | − | 0 | 6 |

Significance probability p = 0.0015

TABLE 3

| | | Periodic variation value (unit: person) | |
|---|---|---|---|
| Rhythm of heart sound | | + | − |
| Brain wave judgment | + | 7 | 3 |
| | − | 0 | 6 |

Significance probability p = 0.011

TABLE 4

| | | Periodic variation value (unit: person) | |
|---|---|---|---|
| Rhythm of electrocardiogram | | + | − |
| Brain wave judgment | + | 6 | 4 |
| | − | 0 | 6 |

Significance probability p = 0.034

TABLE 5

| | | Periodic variation value (unit: person) | |
|---|---|---|---|
| Rhythm of fingertip | | + | − |
| Brain wave judgment | + | 6 | 4 |
| | − | 0 | 6 |

Significance probability p = 0.034

As for the results of comparing the periodic variation values of the all biosignals with the brain wave judgment, significance probability p<0.05 was obtained in a Fisher's exact test. Therefore, there is suggested a high correlation between the brain wave and the rhythm of the biosignal obtained from the frequency gradient time-series waveform.

Further, there are illustrated results of comparing the activity levels of the sympathetic nerve (LF/HF) and the parasympathetic nerve (HF), which were calculated from an electrocardiogram, with the periodic variation value Pv of each biosignal in Table 6. Incidentally, in Table 6, the results of APW, the heart sound, the electrocardiogram, and the finger plethysmogram are all the same, to thus be illustrated by one numerical value. However, the results of comparing the brain wave with the periodic variation values were different, and thus only the result of the brain wave is illustrated in parentheses. As a result of the Fisher's exact test being performed, the probability of inversion in the autonomic nervous system is found to be p=0.04 by a two-sided test, which is significantly high, in the group where the periodic variation values Pv of the biosignals other than the brain wave are in the group of (+), and there is a possibility that the variation of the autonomic nerve activity accompanying the state change from wakefulness to sleep and the rhythm variation of the biosignal obtained from the frequency gradient time-series waveform work simultaneously. Further, many of the subjects exhibited different rhythm cycles at a wakeful time and at a sleep time because Dfw was in a band of 0.003 to 0.0045 Hz and Dfs shifted to a low-frequency side of less than 0.003 Hz. There is a possibility that a long-period region of around 0.003 Hz reflects functions of body temperature regulation, humoral regulation system, and circulation regulation, and it is thought that effects of these physiological regulation functions have appeared as rhythm variations of the "state of resisting against sleepiness while being in a wakeful state" and the "sleep state."

TABLE 6

|  |  | Periodic variation value Pv of each biosignal | |
|---|---|---|---|
|  |  | + | − |
| Autonomic nerve | LF/HF and HF are inverted | 11 (9) | 0 (2) |
|  | HF/HF and HF are not inverted | 2 (2) | 3 (3) |

Value in the parenthesis is a comparison result by brain wave unit: person

Experimental Example 2

In an experimental example 2, a 90-minute sleep-inducing experiment, which is longer than that in the experimental example 1, was performed. Subjects each sat in a reclining chair to be maintained in a sitting position for first 30 minutes, and after 30 minutes, the reclining chair was reclined and the posture was changed to a posture close to a supine position. As criteria for judging the brain wave state, the following criteria were adopted.

Wakeful state: the α wave of the brain wave is 50% or more

Figure 12:
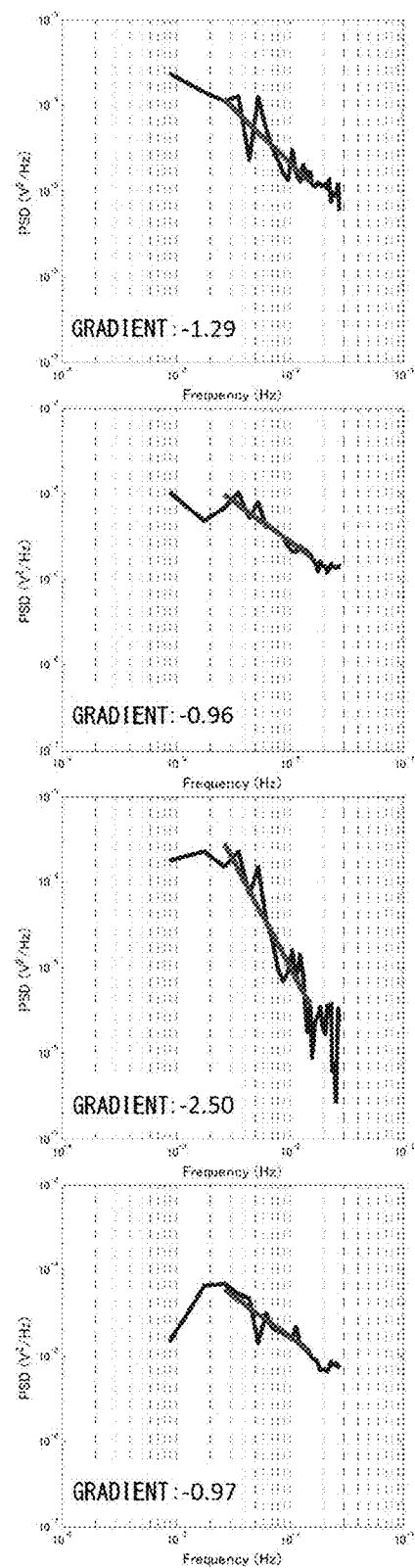
FIG. 12 is charts illustrating an analyzed waveform of an analysis result of a gradient time-series waveform of APW of a subject in an experimental example 2 being output in a log-log graph and its approximate line.
Figure 13:
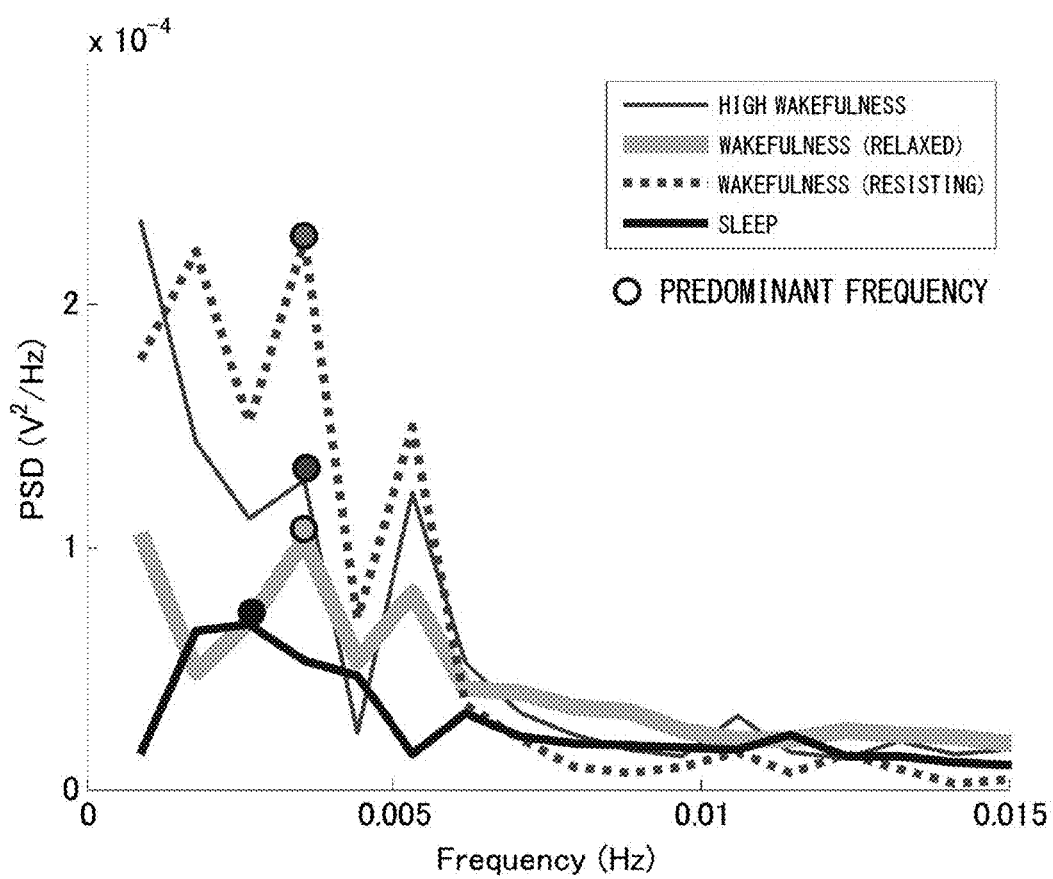
FIG. 13 is a chart illustrating an analyzed waveform of the analysis result of the gradient time-series waveform of APW of the subject in the experimental example 2 being output in a linear graph and its approximate line.
Figure 14:
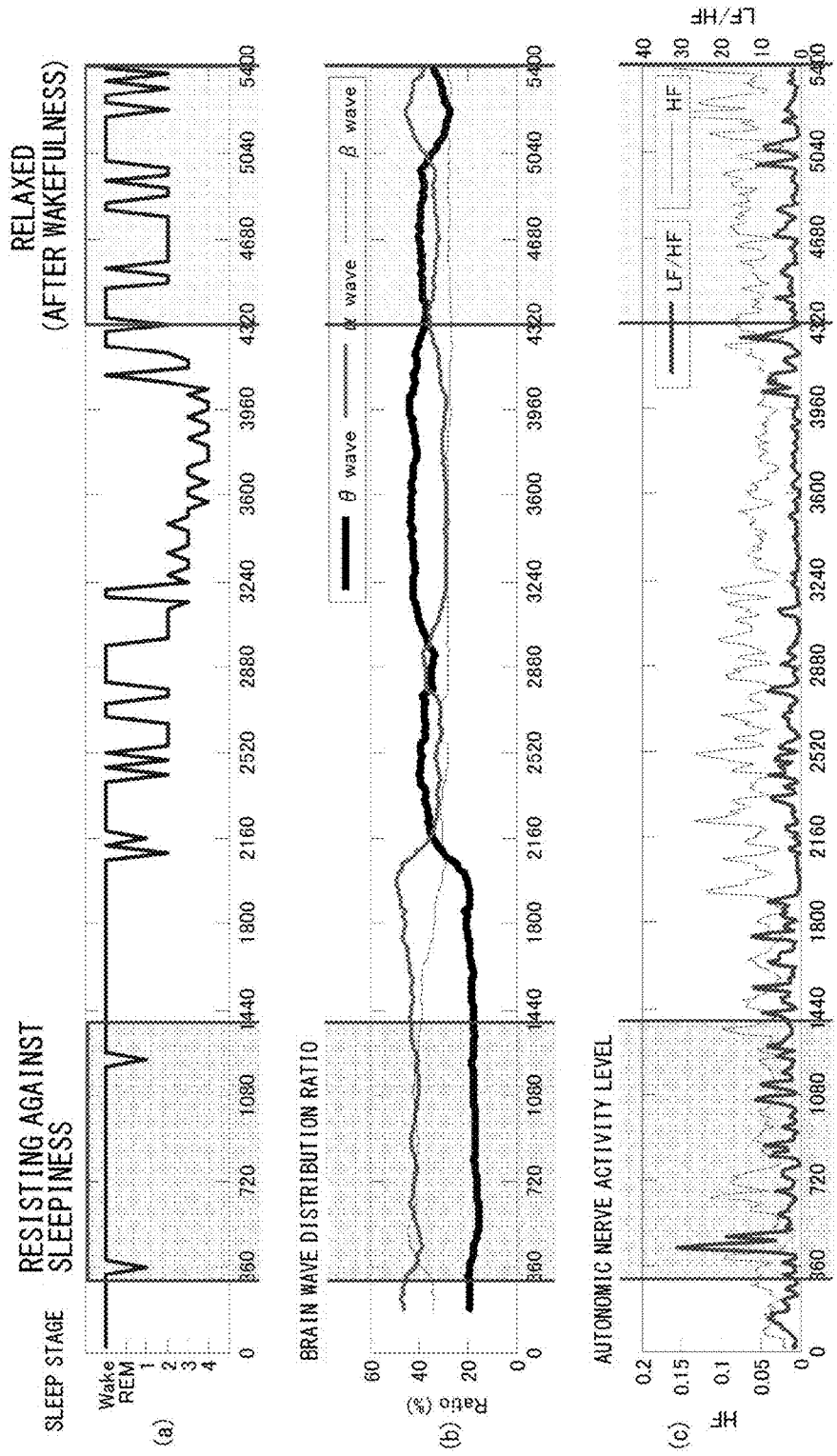
FIGS. 14(a) to (c) are one example of data of the subject in the experimental example 2.
Figure 15:
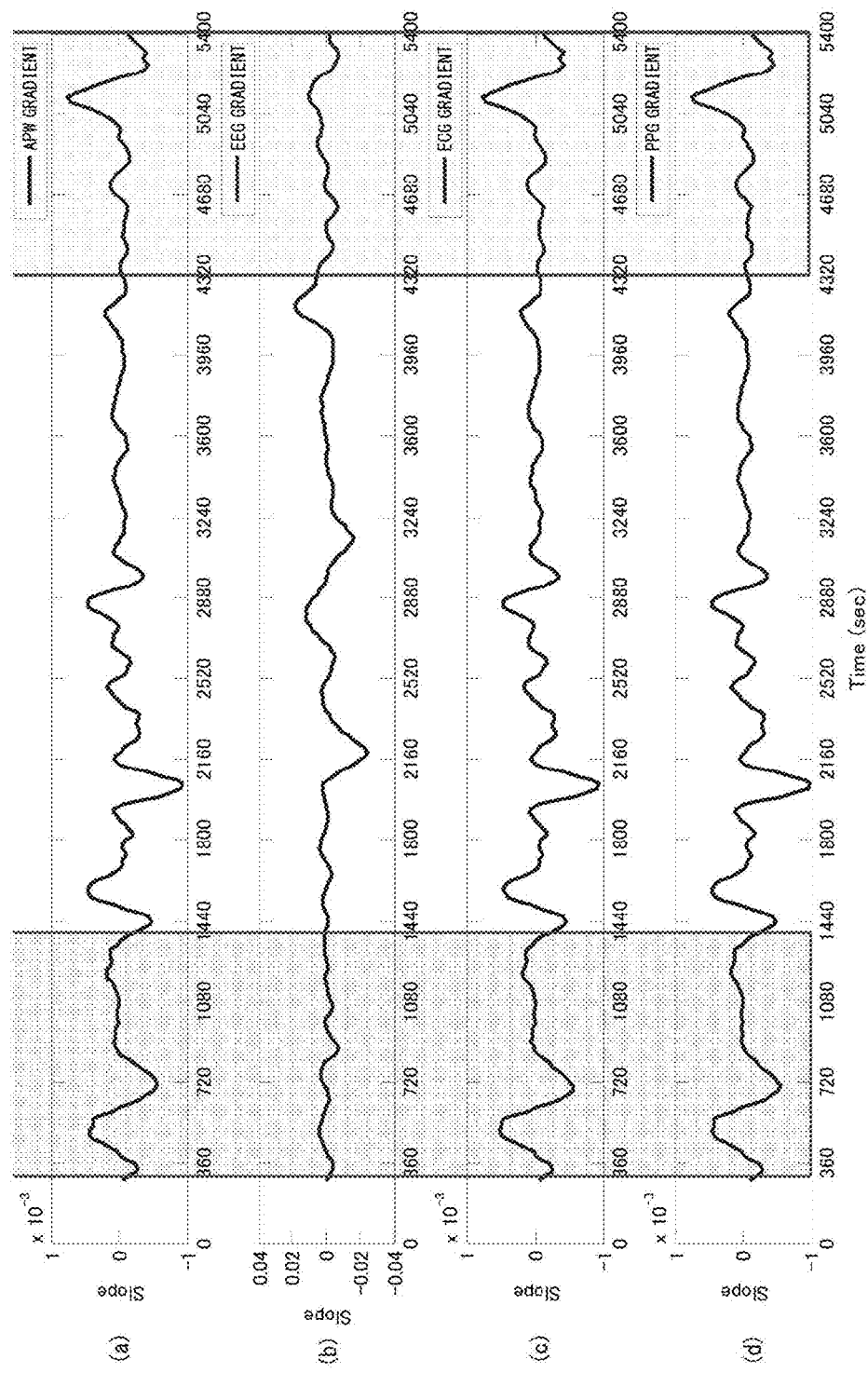
FIGS. 15(a) to (d) illustrate frequency gradient time-series waveforms of biosignals in FIGS. 14(a) to (c)
Figure 16:
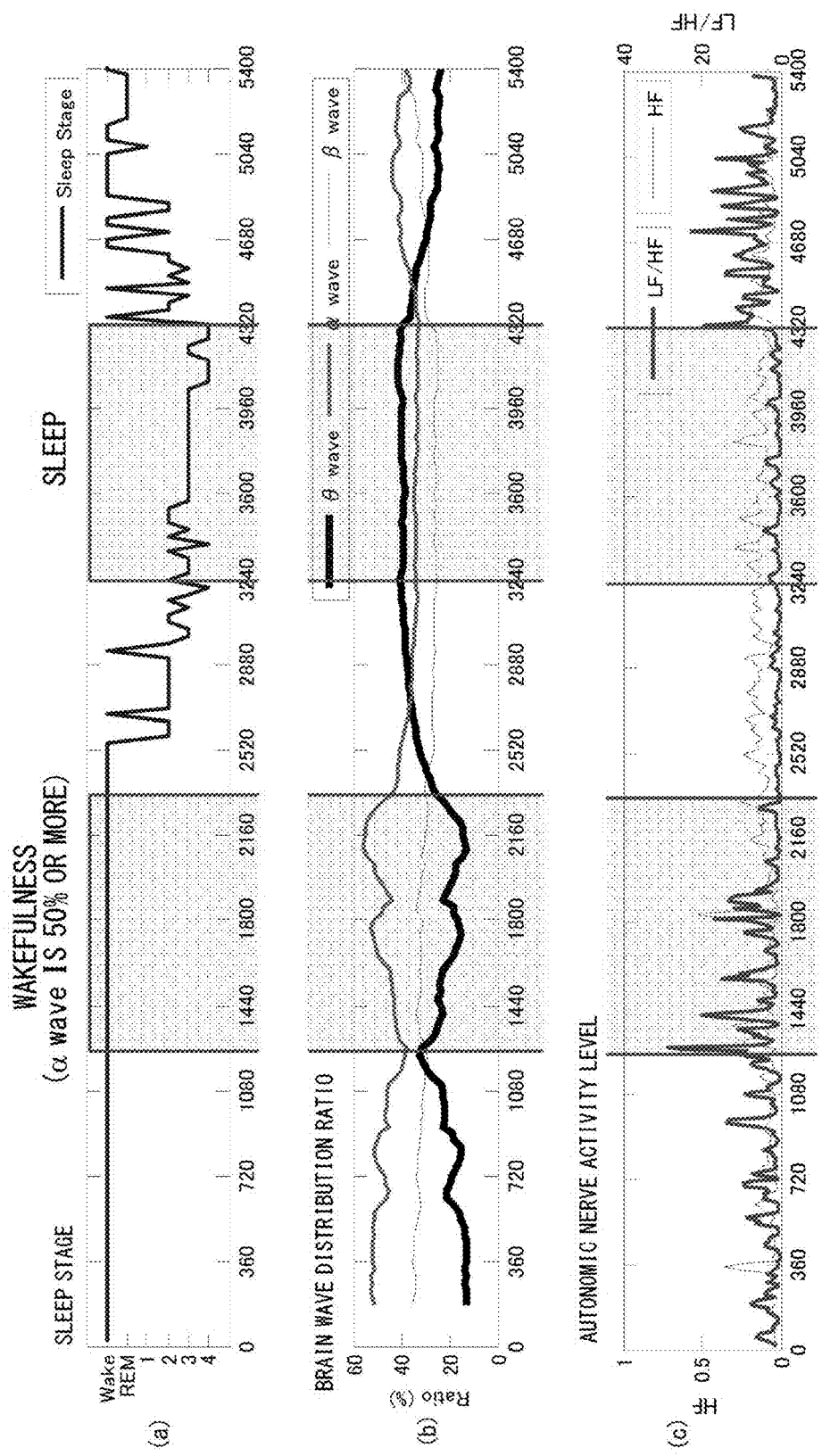
FIGS. 16(a) to (c) are another example of the data of the subject in the experimental example 2.
Figure 17:
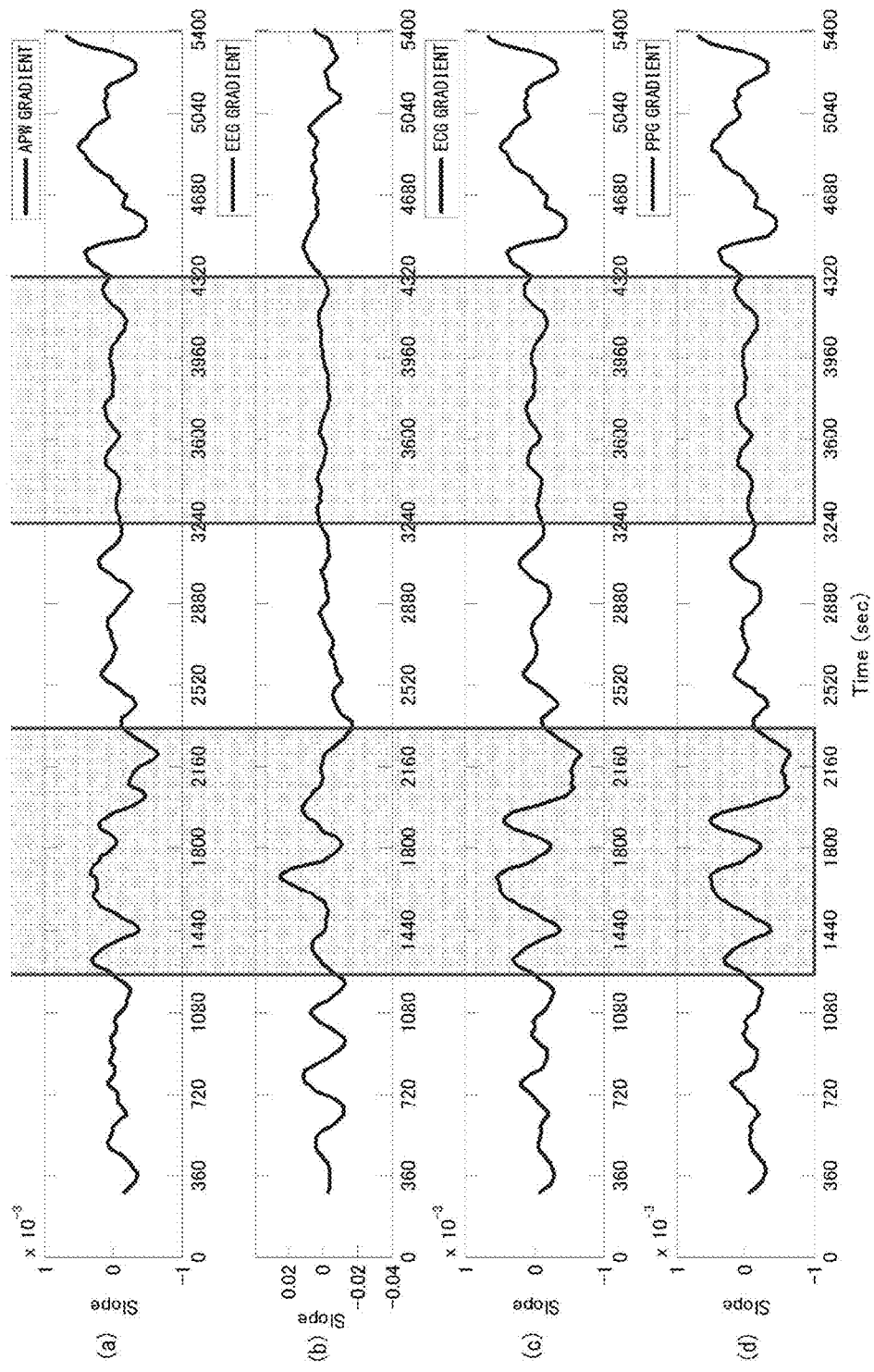
FIGS. 17(a) to (d) illustrate frequency gradient time-series waveforms of biosignals in FIGS. 16(a) to (c)

Relaxed state: the parasympathetic nerve activity accelerates and the α wave of the brain wave increases State of resisting against sleepiness while being in a wakeful state: the sympathetic nerve activity accelerates and of the brain wave, the α wave is 40% or less and the θ wave is 20% or less Sleep state: at sleep stages 2, 3, and 4, of the brain wave, the α wave is 40% or less and the θ wave is 20% or more FIG. 12 illustrates output results by the frequency analysis means 120 displayed in a log-log graph, and FIG. 13 illustrates output results by the frequency analysis means 120 displayed in a linear graph. In FIG. 12 and FIG. 13, data of a 27-year-old male subject, which are illustrated in FIGS. 14(a) to (c) to FIGS. 17(a) to (d), are used. The data in FIGS. 14(a) to (c) and FIGS. 15(a) to (d) and the data in FIGS. 16(a) to (c) and FIGS. 17(a) to (d) are data of the same subject, but are data of the 90-minute sleep-inducing experiments which were performed at different timings. The data in FIGS. 14(a) to (c) and FIGS. 15(a) to (d) are a representative example where the state of resisting against sleepiness while being in a wakeful state occurred before sleep, and the data in FIGS. 16(a) to (c) and FIGS. 17(a) to (d) are a representative example where the subject shifted to sleep from the wakeful state without clear occurrence of the state of resisting against sleepiness.

FIG. 12 reveals that at the wakeful state (high wakeful state where the α wave is 50% or more), the gradient of the approximate line is −1.29, and at the relaxed wakeful state, the gradient of −0.96, which is further approximate to 1/f, is illustrated. At the sleep state as well, the gradient is −0.97 and is approximate to 1/f. In contrast to this, in the state of resisting against sleepiness while being in a wakeful state, the gradient is −2.50 and is approximate to $1/f^2$. Therefore, by seeing the time-series variation of the gradient of the approximate line, that is, in this example, the gradient varies from −1.29 to −0.96, −2.50, and then to −0.97, and thus it is possible to grasp that the state varies from the wakeful state with a high α wave level to the relaxed state, the state of resisting against sleepiness, and then to the sleep state.

FIG. 13 is that the variations in FIG. 12 are represented in a linear graph. It reveals that in each of the high-level wakeful state where the α wave is 50% or more (high wakefulness), the relaxed wakeful state, and the state of resisting against sleepiness while being in a wakeful state, the predominant frequency is around 0.005 Hz, while in the sleep state, the predominant frequency is around 0.0025 Hz. This makes it possible to distinguish the sleep state from the various wakeful states. Further, it is also found out that it is only necessary to see the differences in the power spectrum density of the predominant frequency (amplitude of the predominant frequency) in order to distinguish the high wakefulness, the relaxed wakefulness, and the state of resisting against sleepiness from one another among the wakeful states. That is, the power spectrum density in the state of resisting against sleepiness is the largest, and the power spectrum density in the high wakeful state comes next, and the power spectrum density in the relaxed wakeful state comes next.

Incidentally, according to the present invention, it is possible to detect the "state of resisting against sleepiness while being in a wakeful state" prior to the sleepiness state in particular by APW and the like other than the brain wave with high accuracy. Accordingly, application of the present invention to the biological state estimation device using APW, which is mounted on a driver seat of a vehicle such as an automobile, makes it possible to contribute to increasing the accuracy of detecting a state of driving while feeling very sleepy.

EXPLANATION OF REFERENCE SIGNS 1 biosignal measurement device
11 core pad 12 spacer pad
13 sensor
100 biological state estimation device
110 frequency gradient time-series waveform calculation means
120 frequency analysis means
130 estimation means

The invention claimed is:

1. A biological state estimation device which estimates a biological state by using a biosignal, the biological state estimation device comprising:
a computer processor that performs:
frequency gradient time-series waveform calculation which, from time-series data of the biosignal, obtains a time-series fluctuation of a frequency and obtains a gradient in a predetermined time range of the time-series fluctuation of the frequency, and obtains a time-series fluctuation of the gradient as a frequency gradient time-series waveform;
frequency analysis, which frequency-analyzes the frequency gradient time-series waveform every predetermined time range; and
estimation, which compares an output result of the frequency analysis obtained by the frequency analysis every predetermined time range with preset corresponding data of output results of brain waves of different biological states to the output result of the frequency analysis and estimates a time-series variation of a biological state which is specified by a state of the brain wave and brain waves by means of a time-series variation of the output result of the frequency analysis.

2. The biological state estimation device according to claim 1, wherein
the frequency analysis outputs the result of the frequency analysis in at least one graph of a log-log graph and a linear graph each between frequency and power spectrum density, and
the estimation uses an output result represented by at least one of the log-log graph and the linear graph, compares the output result with the corresponding data of the brain wave, and estimates a biological state which is specified by a state of the brain wave and brain waves.

3. The biological state estimation device according to claim 2, wherein
in the case where the log-log graph is used as an output result of frequency analysis obtained by the frequency analysis, the estimation is set to estimate that the case where an approximate line of an analyzed waveform represented by the log-log graph is approximate to $1/f$ is a "sleep state" where in brain wave distribution ratios, the $\theta$ wave is predominant over the $\alpha$ wave, the $\theta$ wave is equal to or more than predetermined values, and the $\alpha$ wave is equal to or less than predetermined values, and estimate that the case where the approximate line is approximate to $1/f^2$ is a "state of sleepiness strongly resisting while being in a wakeful state" where the $\alpha$ wave or the $\beta$ wave is the same as or predominant over the $\theta$ wave and the distribution ratio of $\beta$ wave is the same as or predominant over the distribution ratio of $\theta$ wave when compared.

4. The biological state estimation device according to claim 2, wherein
in the case where the linear graph is used as an output result of frequency analysis obtained by the frequency analysis, the estimation performs estimation by using a position of a predominant frequency or an amplitude of the predominant frequency in the linear graph.

5. A non-transitory computer storage medium that stores a computer program causing a computer as a biological state estimation device to execute a biological state estimation procedure for estimating a biological state by analyzing a biosignal of a person measured by a biosignal measurement device,
the computer program causing the computer to execute: as the biological state estimation procedure,
a frequency gradient time-series waveform calculation procedure which, from time-series data of the biosignal, obtains a time-series fluctuation of a frequency and obtains a gradient in a predetermined time range of the time-series fluctuation of the frequency, and obtains a time-series fluctuation of the gradient as a frequency gradient time-series waveform;
a frequency analysis procedure which frequency-analyzes the frequency gradient time-series waveform every predetermined time range; and
an estimation procedure which compares an output result of the frequency analysis obtained by the frequency analysis procedure every predetermined time range with corresponding data of output results of brain waves of different biological states to the output result of the frequency analysis, which are stored in the computer beforehand, and estimates a time-series variation of a biological state which is specified by a state of the brain wave and brain waves by means of a time-series variation of the output result of the frequency analysis.

6. The non-transitory computer storage medium according to claim 5, wherein
the frequency analysis procedure outputs the result of the frequency analysis in at least one graph of a log-log graph and a linear graph each between frequency and power spectrum density, and
the estimation procedure uses an output result represented by at least one of the log-log graph and the linear graph, compares the output result with the corresponding data of the brain wave, and estimates a biological state which is specified by a state of the brain wave and brain waves.

7. The non-transitory computer storage medium according to claim 6, wherein
in the case where the log-log graph is used as an output result of frequency analysis obtained by execution of the frequency analysis procedure, the estimation procedure estimates that the case where an approximate line of an analyzed waveform represented by the log-log graph is approximate to $1/f$ is a "sleep state" where in brain wave distribution ratios, the $\theta$ wave is predominant over the $\alpha$ wave, the $\theta$ wave is equal to or more than predetermined values, and the $\alpha$ wave is equal to or less than predetermined values, and estimates that the case where the approximate line is approximate to $1/f^2$ is a "state of sleepiness strongly resisting while being in a wakeful state" where the $\alpha$ wave or the $\beta$ wave is the same as or predominant over the $\theta$ wave and the distribution ratio of $\beta$ wave is the same as or predominant over the distribution ratio of $\theta$ wave when compared.

8. The non-transitory computer storage medium according to claim 6, wherein
in the case where the linear graph is used as an output result of frequency analysis obtained by execution of the frequency analysis procedure, the estimation procedure performs estimation by using a position of a predominant frequency or an amplitude of the predominant frequency in the linear graph.

9. A biological state estimation method which estimates a biological state by using a biosignal, the method comprising:

from time-series data of the biosignal, obtaining a time-series fluctuation of a frequency and obtaining a gradient in a predetermined time range of the time-series fluctuation of the frequency, and obtaining a time-series fluctuation of the gradient as a frequency gradient time-series waveform;

frequency-analyzing the frequency gradient time-series waveform every predetermined time range; and comparing an output result of the frequency analysis obtained every predetermined time range with preset corresponding data of output results of brain waves of different biological states to the output result of the frequency analysis and estimating a time-series variation of a biological state which is specified by a state of the brain wave and brain waves by means of a time-series variation of the output result of the frequency analysis.

10. The biological state estimation method according to claim 9, wherein the result of the frequency analysis is output in at least one graph of a log-log graph and a linear graph each between frequency and power spectrum density, and an output result represented by at least one of the log-log graph and the linear graph is used, to compare the output result with the corresponding data of the brain wave and estimate a biological state which is specified by a state of the brain wave and brain waves.

11. The biological state estimation method according to claim 10, wherein in the case where the log-log graph is used as an output result of the frequency analysis, the case where an approximate line of an analyzed waveform represented by the log-log graph is approximate to $1/f$ is estimated as a "sleep state" where in brain wave distribution ratios, the $\theta$ wave is predominant over the $\alpha$ wave, the $\theta$ wave is equal to or more than predetermined values, and the $\alpha$ wave is equal to or less than predetermined values, and the case where the approximate line is approximate to $1/f^2$ is estimated as a "state of sleepiness strongly resisting while being in a wakeful state" where the $\alpha$ wave or the $\beta$ wave is the same as or predominant over the $\theta$ wave and the distribution ratio of $\beta$ wave is the same as or predominant over the distribution ratio of $\theta$ wave when compared.

12. The biological state estimation method according to claim 10, wherein in the case where the linear graph is used as an output result of the frequency analysis, estimation is performed by using a position of a predominant frequency or an amplitude of the predominant frequency in the linear graph.

* * * * *